US012083067B2

(12) United States Patent
Behboodi et al.

(10) Patent No.: US 12,083,067 B2
(45) Date of Patent: Sep. 10, 2024

(54) MODULAR ARTIFICIAL SKELETAL MUSCLE ACTUATORS AND EXOSKELETONS POWERED THEREBY

(71) Applicants: Ahad Behboodi, Newark, DE (US); Samuel C. K. Lee, Fork, MD (US); Stuart A. Binder-Macleod, Newark, DE (US); Henry Wright, Lincoln University, PA (US)

(72) Inventors: Ahad Behboodi, Newark, DE (US); Samuel C. K. Lee, Fork, MD (US); Stuart A. Binder-Macleod, Newark, DE (US); Henry Wright, Lincoln University, PA (US)

(73) Assignee: University of Delaware, Newark, DE (US)

( * ) Notice: Subject to any disclaimer, the term of this patent is extended or adjusted under 35 U.S.C. 154(b) by 819 days.

(21) Appl. No.: 17/117,904

(22) Filed: Dec. 10, 2020

(65) Prior Publication Data

US 2021/0121355 A1    Apr. 29, 2021

Related U.S. Application Data

(63) Continuation-in-part of application No. PCT/US2019/037250, filed on Jun. 14, 2019.
(Continued)

(51) Int. Cl.
*A61H 3/00* (2006.01)
*A61F 5/01* (2006.01)

(52) U.S. Cl.
CPC .............. *A61H 3/00* (2013.01); *A61F 5/0127* (2013.01); *A61H 2201/1207* (2013.01);
(Continued)

(58) Field of Classification Search
CPC .............. A61H 3/00; A61H 2201/1207; A61H 2201/1642; A61H 2201/1652;
(Continued)

(56) References Cited

U.S. PATENT DOCUMENTS

| 6,379,393 B1 | 4/2002 | Mavroidis et al. |
| 2009/0085444 A1 | 4/2009 | Rivera et al. |

(Continued)

FOREIGN PATENT DOCUMENTS

WO    2018023109 A1    2/2018

OTHER PUBLICATIONS

Acome et al., "Hydraulically amplified self-healing electrostatic actuators with muscle-like performance" Science 359, 61-65 (2018), 5 pages.
(Continued)

*Primary Examiner* — Rachel T Sippel
*Assistant Examiner* — Jacqueline M Pinderski
(74) *Attorney, Agent, or Firm* — Buchanan Ingersoll & Rooney PC

(57) ABSTRACT

A modular artificial skeletal muscle (MASM) actuator having a plurality of dielectric elastomer units assembled in series or in parallel. A proximal anchoring member is connected to a proximal end of at least one proximal dielectric elastomer unit and is configured for attachment to a proximal anchor point relative to a user. A tension member has a proximal end attached to a distal end of at least one distal dielectric elastomer unit and a distal end configured for attachment to a distal anchor point relative to the user. A controller is configured to cause simultaneous contraction or expansion of plurality of dielectric elastomer units, which contraction or expansion causes displacement of the tension member. A plurality of MASM actuators may be attached to an exoskeleton attached about an ankle of a user and
(Continued)

controlled for therapeutic purposes, such as for assisting pediatric patients with cerebral palsy.

34 Claims, 17 Drawing Sheets

Related U.S. Application Data

(60) Provisional application No. 62/947,949, filed on Dec. 13, 2019, provisional application No. 62/745,512, filed on Oct. 15, 2018, provisional application No. 62/684,908, filed on Jun. 14, 2018.

(52) U.S. Cl.
CPC .............. *A61H 2201/1642* (2013.01); *A61H 2201/1652* (2013.01); *A61H 2203/0406* (2013.01); *A61H 2205/06* (2013.01); *A61H 2205/12* (2013.01); *A61H 2230/085* (2013.01)

(58) Field of Classification Search
CPC ........ A61H 2203/0406; A61H 2205/06; A61H 2205/12; A61H 2230/085; A61H 1/0277; A61H 2201/1638; A61H 2201/5058; A61H 2201/5084; A61H 1/0237; A61H 1/0266; A61H 2201/50; A61H 2230/605; A61H 1/00; A61F 5/0127; B25J 9/0006
See application file for complete search history.

(56) References Cited

U.S. PATENT DOCUMENTS

| | | | |
|---|---|---|---|
| 2012/0161579 A1 | 6/2012 | Browne et al. | |
| 2013/0085433 A1 | 4/2013 | Grant et al. | |
| 2014/0277739 A1 | 9/2014 | Kornbluh et al. | |
| 2016/0107309 A1* | 4/2016 | Walsh ................ | A63B 21/0054 248/550 |
| 2016/0184141 A1 | 6/2016 | Zelka | |
| 2016/0338207 A1* | 11/2016 | Zelka ................... | H05K 3/0044 |
| 2018/0248497 A1* | 8/2018 | Hendriks ............. | H02N 11/006 |

OTHER PUBLICATIONS

Babik et al., "Feasibility and Effectiveness of a Novel Exoskeleton for an Infant with Arm Movement Impairments", Pediatr. Phys. Ther., 2016; 28(3): 338-346.
Bar-Cohen et al., "Biologically inspired intelligent robots", Proc. SPIE 5051, Smart Structures and Materials 2003: Electroactive Polymer Actuators and Devices (EAPAD), (Jul. 28, 2003), 8 pages.
Behboodi et al., "Seven phases of gait detected in real-time using shank attached gyroscopes", Annual International Conference of the IEEE Engineering in Medicine and Biology Society. IEEE Engineering in Medicine and Biology Society. Conference, Aug. 2016, 5 pages.
Behboodi, A., "An Artificial Skeletal Muscle for use in Pediatric Rehabilitation Robotics", A dissertation submitted to the Faculty of the University of Delaware in partial fulfillment of the requirements for the degree of Doctor of Philosophy in Biomechanics and Movement Science, Summer 2019, 147 pages.
Biddiss et al., "Dielectric elastomers as actuators for upper limb prosthetics: Challenges and opportunities", Medical Engineering & Physics 30 (2008) 403-418.
Brackbill et al., "Dynamics and Control of a 4-dof Wearable Cable-driven Upper Arm Exoskeleton", 2009 IEEE International Conference on Robotics and Automation Kobe International Conference Center Kobe, Japan, May 12-17, 2009, 6 pages.
Calabro et al., "Who May Benefit From Armeo Power Treatment? A Neurophysiological Approach to Predict Neurorehabilitation Outcomes", PM R 8 (2016) 971-978.

Carpi et al., "Elastomeric contractile actuators for hand rehabilitation splints", Proc. SPIE 6927, Electroactive Polymer Actuators and Devices (EAPAD) 2008, 692705 (Apr. 29, 2008), 11 pages.
Carpi et al., "Electroactive polymer actuators as artificial muscles: are they ready for bioinspired applications?", Bioinspir. Biomim., 2011. 6 045006, 11 pages.
Carpi et al., "Enabling variable-stiffness hand rehabilitation orthoses with dielectric elastomer transducers", Medical Engineering & Physics 36(2014) 205-211.
Carpi et al., "Helical dielectric elastomer actuators", Smart Mater. Struct., 14(2005) 1210-1216.
Carpi et al., "Real-time control of dielectric elastomer actuators via bioelectric and biomechanical signals", Polym. Int., 2010; 59: 422-429.
Carpi et al., "Stretching Dielectric Elastomer Performance", Science, vol. 330, Dec. 24, 2010, 4 pages.
Carpi et al., "Wearable Sensory-Motor Orthoses for Tele-Rehabilitation", Proceedings of the 25th Annual International Conference of the IEEE EMBS Cancun, Mexico, Sep. 17-21, 2003, 4 pages.
Chuc et al., "A dielectric elastomer actuator with self-sensing capability", Proc. SPIE 6927. Electroactive Polymer Actuators and Devices (EAPAD) 2008. 69270V (Apr. 10, 2008), 9 pages.
Chuc et al., "Multi-stacked Artificial Muscle Actuator Based on Synthetic Elastomer", Proceedings of the 2007 IEEE/RSJ International Conference on Intelligent Robots and Systems San Diego, CA, USA, Oct. 29, Nov. 2, 2007, 771-776.
Dollar et al., "Lower Extremity Exoskeletons and Active Orthoses: Challenges and State-of-the-Art", IEEE Transactions on Robotics, vol. 24. . No. 1, Feb. 2008, 144-158.
Fasoli et al., "New Horizons for Robot-Assisted Therapy in Pediatrics", Am. J. Phys. Med. Rehabil., vol. 91, No. 11 (Suppl), Nov. 2012, 10 pages.
Gisby et al., "An adaptive control method for dielectric elastomer devices", Proc. SPIE 6927, Electroactive Polymer Actuators and Devices (EAPAD) 2008, 69271C (Apr. 10, 2008), 9 pages.
Gisby et al., "Closed loop control of dielectric elastomer actuators", Proc. SPIE 7976, Electroactive Polymer Actuators and Devices (EAPAD) 2011, 797620 (Mar. 28, 2011), 10 pages.
Gisby et al., "Self sensing feedback for dielectric elastomer actuators", Appl. Phys. Lett. 102, 193703 (2013), 5 pages.
Gopura et al., "Developments in hardware systems of active upper-limb exoskeleton robots: A review", Robotics and Autonomous Systems (2015), 18 pages.
Gurunathan et al., "Electrochemically synthesised conducting polymeric materials for applications towards technology in electronics, optoelectronics and energy storage devices", Materials Chemistry and Physics 61 (1999) 173-191.
Ha et al., "Interpenetrating Polymer Networks for High-Performance Electroelastomer Artificial Muscles", Adv. Mour., 2006, 78, 887-891.
Hall et al., "Design and development of the first exoskeletal garment to enhance arm mobility for children with movement impairments", Assistive Technology. 2018, vol. 30, No. 5, 251-258.
Hau et al., "A novel dielectric elastomer membrane actuator concept for high-force applications", Extreme Mechanics Letters, Jul. 2018, 8 pages.
Hau et al., "Design and Control of a High-Speed Positioning System Based on Dielectric Elastomer Membrane Actuators", IEEE/ASME Transactions on Mechatronics, vol. 22, No. 3, Jun. 2017, 1259-1267.
Haumont et al., "Wilmington Robotic Exoskeleton: A Novel Device to Maintain Arm Improvement in Muscular Disease", J. Pediatr. Orthop., vol. 31, No. 5, Jul./Aug. 2011, 6 pages.
Herr et al., "New horizons for orthotic and prosthetic technology: artificial muscle for ambulation", Proc. SPIE 5385, Smart Structures and Materials 2004: Electroactive Polymer Actuators and Devices (EAPAD), (Jul. 27, 2004), 10 pages.
Hodgins et al., "An electro-mechanically coupled model for the dynamic behavior of a dielectric electro-active polymer actuator", Smart Mater. Struct., 23 (2014) 104006, 13 pages.
Hodgins et al., "High Frequency Dynamic Model of a Pre-Loaded Circular Dielectric Electro-Active Polymer Actuator", Proceedings

(56) References Cited

OTHER PUBLICATIONS of the ASME 2013 Conference on Smart Materials, Adaptive Structures and Intelligent Systems SMASIS2013, Sep. 16-18, 2013, Snowbird, Utah, USA, 10 pages.
Hodgins et al., "Modeling and experimental validation of a bi-stable out-of-plane DEAP actuator system", Smart Mater. Struct., 20 (2011) 094012, 12 pages.
Hoffstadt et al., "Adaptive Sliding-Mode Position Control for Dielectric Elastomer Actuators", IEEE/ASME Transactions on Mechatronics, vol. 22, No. 5, Oct. 2017, 11 pages.
Hoffstadt et al., "Online identification algorithms for integrated dielectric electroactive polymer sensors and self-sensing concepts", Smart Mater, Struct., 23 (2014) 104007, 14 pages.
Hoffstadt et al., "Self-sensing Algorithms for Dielectric Elastomer Multilayer Stack-Transducers", IFAC-PapersOnLine 49-21 (2016) 373-379.
Hogan et al., "MIT-MANUS : A Workstation for Manual Therapy and Training I", IEEE International Workshop on Robot and Human Communication, 1992, 5 pages.
Jung et al., "A self-sensing dielectric elastomer actuator", Sensors and Actuators A 143 (2008) 343-351.
Keller et al., "ChARMin: The First Actuated Exoskeleton Robot for Pediatric Arm Rehabilitation", IEEE/ASME Transactions on Mechatronics, vol. 21, No. 5, Oct. 2016, 13 pages.
Kim et al., "Combined Clinic-Home Approach for Upper Limb Robotic Therapy After Stroke: A Pilot Study", Archives of Physical Medicine and Rehabilitation 2015, 96:2243-8.
Kohl et al., "A novel actuation mechanism on the basis of ferromagnetic SMA thin films", Sensors and Actuators A 114 (2004) 445-450.
Kornbluh et al., "Rubber to rigid, clamped to undamped: toward composite materials with wide-range controllable stiffness and damping", Proc. SPIE 5388, Smart Structures and Materials 2004: Industrial and Commercial Applications of Smart Structures Technologies, (Jul. 29, 2004), 16 pages.
Kovacs et al., "Stacked dielectric elastomer actuator for tensile force transmission", Sensors and Actuators A 155 (2009) 299-307.
Kovacs et al., "Study on core free rolled actuator based on soft dielectric EAP", Proc. SPIE 6927, Electroactive Polymer Actuators and Devices (EAPAD) 2008, 69270X (Apr. 10, 2008). 16 pages.
Krebs et al., "Rehabilitation robotics: pilot trial of a spatial extension for MIT-Manus", Journal of NeuroEngineering and Rehabilitation 2004, 1:5, 15 pages.
Kwakkel et al., "Effects of Robot-Assisted Therapy on Upper Limb Recovery After Stroke: A Systematic Review", Neurorehabilitation and Neural Repair 22(2); 2008, 11 pages.
Lobo et al., "Grounding Early Intervention: Physical Therapy Cannot Just Be About Motor Skills Anymore", Physical Therapy, vol. 93, No. 1, 10 pages.
Lum et al., "MIME robotic device for upper-limb neurorehabilitation in subacute stroke subjects: A follow-up study", Journal of Rehabilitation Research & Development. vol. 43, No. 5, Aug./Sep. 2006, pp. 631-642.
Maciejasz et al., "A survey on robotic devices for upper limb rehabilitation", Journal of NeuroEngineering and Rehabilitation, 2014, 11:3, 29 pages.
Madden et al., "Artificial Muscle Technology: Physical Principles and Naval Prospects", IEEE Journal of Oceanic Engineering, vol. 29, No. 3, Jul. 2004, 23 pages.
Mao et al., "Design of a Cable-Driven Arm Exoskeleton (CAREX) for Neural Rehabilitation", IEEE Transactions on Robotics, vol. 28, No. 4, Aug. 2012, 10 pages.
Mirfakhrai et al., "Polymer Artificial Muscles", MaterialsToday, Apr. 2007, vol. 10, No. 4, 9 pages.
Needham et al., "A pick-me-up for infants' exploratory skills: Early simulated experiences reaching for objects using 'sticky mittens' enhances young infants' object exploration skills", Infant Behavior & Development 25 (2002) 279-295.
Nef et al., "ARMin—Exoskeleton Robot for Stroke Rehabilitation", IFMBE Proceedings 25/1X, 2009, pp. 127-130.
Nef et al., "ARMin III—arm therapy exoskeleton with an ergonomic shoulder actuation", Applied Bionics and Biomechanics, vol. 6, No. 2, Jun. 2009, 127-142.
Nef et al., "ARMin—Design of a Novel Arm Rehabilitation Robot", Proceedings of the 2005 IEEE 9th International Conference on Rehabilitation Robotics, Jun. 28-Jul. 1, 2005, Chicago, IL, USA, 4 pages.
Nef et al., "ARMin—Exoskeleton for Arm Therapy in Stroke Patients", Proceedings of the 2007 IEEE 10th International Conference on Rehabilitation Robotics, Jun. 12-15. Noordwijk, The Netherlands, 7 pages.
Nef et al., "ARMin: a robot for patient-cooperative arm therapy", Med. Bio. Eng. Compul., (2007) 45:887-900.
Page et al., "Portable upper extremity robotics is as efficacious as upper extremity rehabilitative therapy: a randomized controlled pilot trial", Clinical Rehabilitation 27(6) 494-503.
Pel et al., "Multifunctional electroelastomer rolls and their application for biomimetic walking robots", Proc. SPIE 4698, Smart Structures and Materials 2002: Industrial and Commercial Applications of Smart Structures Technologies, (Jul. 9, 2002), 9 pages.
Qian et al., "Recent Development of Rehabilitation Robots", Advances in Mechanical Engineering, 2014, 11 pages.
Ragonesi et al., "Series Elastic Actuator Control of a Powered Exoskeleton", 33rd Annual International Conference of the IEEE EMBS Boston, Massachusetts USA, Aug. 30-Sep. 3, 2011, 4 pages.
Rahman et al. "Design and Testing of a Functional Arm Orthosis in Patients With Neuromuscular Diseases", IEEE Transactions on Neural Systems and Rehabilitation Engineering, vol. 15, No. 2, Jun. 2007, 8 pages.
Rahman et al., "Development and Testing of a Modular Upper Extremity Exoskeleton for Infants", Proceedings of the International Conference on Biomedical Electronics and Devices (TPDULL-2014), pp. 316-319.
Reinkensmeyer et al., "Technologies and combination therapies for enhancing movement training for people with a disability", Journal of NeuroEngineering and Rehabilitation 2012. 9:17, 10 pages.
Renda et al., "Dynamic Model of a Multibending Soft Robot Arm Driven by Cables", IEEE Transactions on Robotics, vol. 30, No. 5, Oct. 2014, 14 pages.
Rizzello et al., "Closed loop control of dielectric elastomer actuators based on self-sensing displacement feedback", Smart Mater, Struct., 25 035034, 2016, 14 pages.
Rizzello et al., "Model-based PID control of a Dielectric Electro-Active Polymer Positioning System", Proceedings of the 19th World Congress, The International Federation of Automatic Control Cape Town, South Africa. Aug. 24-29, 2014, 8 pages.
Rizzello et al., "Robust Position Control of Dielectric Elastomer Actuators Based on LMI Optimization", IEEE Transactions on Control Systems Technology, vol. 24, No. 6, Nov. 2016, 13 pages.
Rocon et al., "Rehabilitation Robotics: a Wearable Exo-Skeleton for Tremor Assessment and Suppression", Proceedings of the 2005 IEEE International Conference on Robotics and Automation Barcelona, Spain, Apr. 2005, 6 pages.
Rosset et al., "Self-sensing dielectric elastomer actuators in closed-loop operation", Smart Mater. Struct., 22 (2013) 104018, 11 pages.
Rus et al., "Design, fabrication and control of soft robots", Nature, vol. 521, May 28, 2015, 10 pages.
Sanchez et al., "A Pneumatic Robot for Re-Training Arm Movement after Stroke: Rationale and Mechanical Design", Proceedings of the 2005 IEEE 9th International Conference on Rehabilitation Robotics Jun. 28-Jul. 1, 2005, Chicago, IL, USA, 5 pages.
Sarban et al., "A tubular dielectric elastomer actuator: Fabrication, characterization and active vibration isolation", Mechanical Systems and Signal Processing 25 (2011) 2879-2891.
Shorter et al., "Technologies for Powered Ankle-Foot Orthotic Systems: Possibilities and Challenges", IEEE/ASME Transactions on Mechatronics, vol. 18, No. 1, Feb. 2013, 11 pages.
Stein et al., "Electromyography-Controlled Exoskeletal Upper-Limb-Powered Orthosis for Exercise Training After Stroke", Am. J. Phys. Med. Rehabil., 2007; 86:255-261.
Vallery et al., "Compliant Actuation of Rehabilitation Robots", IEEE Robotics & Automation Magazine, Sep. 2008, 10 pages.

(56) References Cited

OTHER PUBLICATIONS

Weinman, K., "Smart polymers transform electrical energy into mechanical work", Editor Media Contact, Jul. 11, 2018, 3 pages.
Ye et al., "Integrated sensing and actuation of dielectric elastomer actuator", Proc. SPIE 10163, Electroactive Polymer Actuators and Devices (EAPAD) 2017, 101630C (Apr. 17, 2017), 9 pages.
Yoo et al., "Artificial Muscles, Made of Dielectric Elastomer Actuators—A Promising Solution for Inherently Compliant Future Robots", Soft Robotics, 2015, 33-41.
Zhang et al., "Dielectric Elastomer Spring Roll Actuators for a Portable Force Feedback Device", Symposium on Haptic Interfaces for Virtual Environment and Teleoperator Systems Mar. 25-26, 2006, Alexandria, Virginia, USA, 7 pages.
Zrinyi et al., "Intelligent polymer gels controlled by magnetic fields", Colloid Polym. Sci., (2000) 278:98-103.
International Preliminary Report on Patentability for International Application PCT/US2019/037250, dated Dec. 15, 2020, 9 pages.
International Search Report and Written Opinion for International Application No. PCT/US2019/037250, dated Sep. 11, 2019, 10 pages.
Carpi et al., "Contractile dielectric elastomer actuator with folded shape", Proc. SPIE 6168, Smart Structures and Materials 2006: Electroactive Polymer Actuators and Devices (EAPAD), 61680D, Mar. 17, 2006, 7 pages.
Carpi et al., "Folded dielectric elastomer actuators", 2007 Smart Mater. Struct. 16 S300, 7 pages.
Galantini et al., "Effects of plasticization of a soft silicone for dielectric elastomer actuation", 11 pages.
Rahman et al., "Design and Testing of WREX", Advances in Rehabilitation Robotics, LNCIS 306, pp. 243-250, 2004.

\* cited by examiner

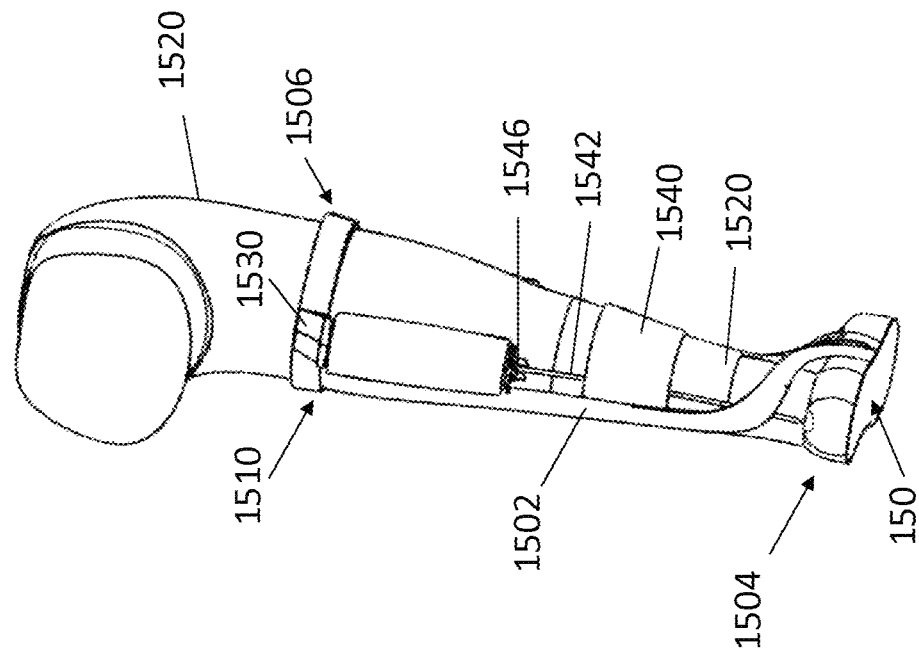
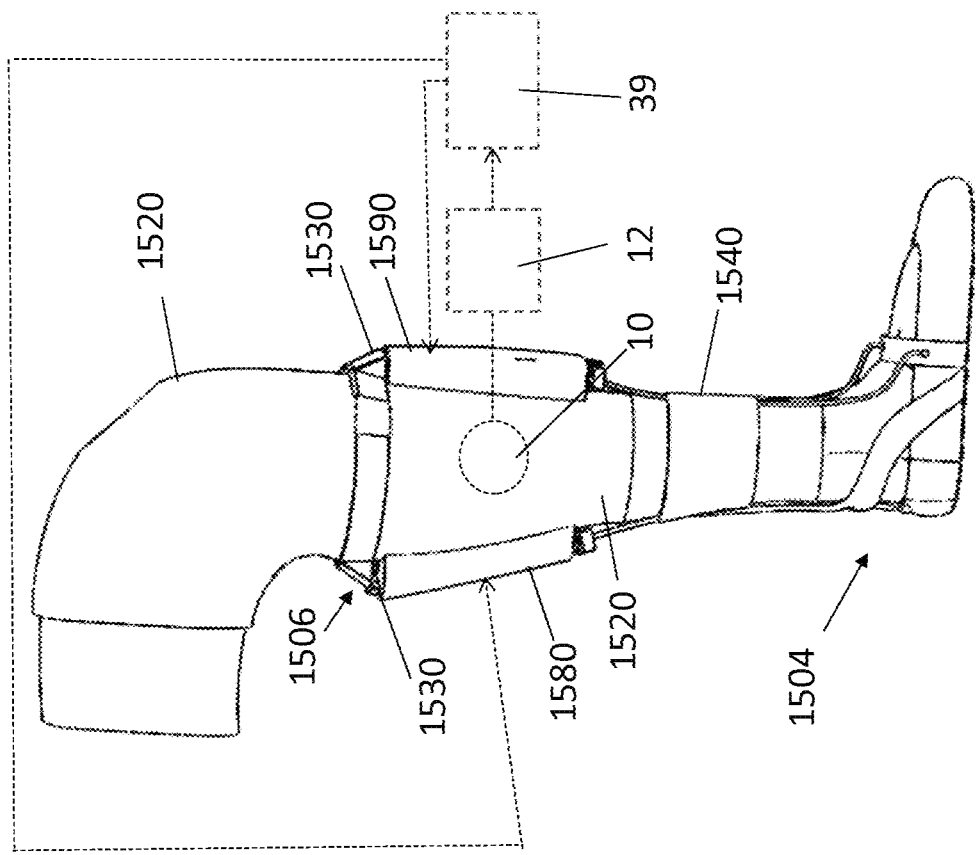
FIG. 15D
FIG. 15C

MODULAR ARTIFICIAL SKELETAL MUSCLE ACTUATORS AND EXOSKELETONS POWERED THEREBY

CROSS REFERENCE TO RELATED APPLICATIONS

This application claims priority from U.S. Provisional Application Ser. No. 62/947,949, filed Dec. 13, 2019. This application is also a continuation-in-part of PCT Application Ser. No. U.S. Ser. No. 19/037,250, filed Jun. 14, 2019. Both of the foregoing are titled MODULAR ARTIFICIAL SKELETAL MUSCLE ACTUATORS AND EXOSKELETONS POWERED THEREBY. PCT Application Ser. No. U.S. Ser. No. 19/037,250 claims priority from U.S. Provisional Application Ser. No. 62/684,908, filed Jun. 14, 2018, and from U.S. Provisional Application Ser. No. 62/745,512, filed Oct. 15, 2018, both titled "AMPEX, Artificial Muscle Powered Exoskeleton." The contents of all of the foregoing are hereby incorporated by reference.

STATEMENT REGARDING FEDERALLY SPONSORED RESEARCH

This invention was made with government support under Grant Number U54-GM104941 awarded by the National Institute of Health (NIH) to Delaware-CTR ACCEL (Accelerating Clinical and Translational Research). The government has certain rights in the invention.

BACKGROUND OF THE INVENTION

To improve the acceptability and performance of rehabilitation robots, development of actuator technology with natural feel is highly desirable. For exoskeleton applications, it is desirable for the actuator to have force and displacement generation comparable to that of mammalian skeletal muscle. Actuators that are soft, noiseless, have linear actuation, and produce comparable force and displacement to skeletal muscle are referred to as artificial skeletal muscles.

Soft electroactive polymer actuators, such as dielectric elastomer actuators (DEAs), are fast, efficient and offer a lightweight and acoustically noiseless alternative to DC motor actuators used in conventional rehabilitation robotic systems. Dielectric elastomer actuators comprise a compliant capacitor, namely an elastic dielectric sandwiched between two mechanically compliant electrodes There are two main DEA configurations: 1) freestanding DEAs and 2) DEAs with rigid frames. Rigid frames may not be ideal where soft actuators are preferable. Consequently, in artificial skeletal muscle applications, freestanding configurations offer more natural feel to the design. Various freestanding configurations are known, including stacked, folded, helical, membrane, and spring roll DEAs, as shown in FIG. 1. Stacked DEAs have shown the most similarity to human skeletal muscle compared with other linear DEA configurations, and have shown a capability of producing 32N of isometric force and 15% strain while lifting a 1.1 Kg tensile load.

A commercially available Stacked DEA, depicted in FIG. 2, is manufactured by CTsystems of Dubendorf, Switzerland.

SUMMARY OF THE INVENTION

One aspect of the invention comprises a modular artificial skeletal muscle (MASM) actuator. The MASM actuator includes a plurality of dielectric elastomer units assembled in series or in parallel. A proximal anchoring member is connected to a proximal end of at least one proximal dielectric elastomer unit and configured for attachment to a proximal anchor point relative to a user. A proximal end of a tension member, such as a flexible, non-extendable cable, is attached to a distal end of at least one distal dielectric elastomer unit. A distal end of the tension member is configured for attachment to a distal anchor point relative to the user. A controller attached to a power source and to the plurality of dielectric elastomer units is configured to cause simultaneous contraction or expansion of plurality of dielectric elastomer units, which contraction or expansion causes displacement of the tension member. The MASM actuator may have a flexible, low friction covering, which also acts as an electrical insulator, disposed over an external surface of the plurality of dielectric elastomer units. A self-sensing circuit connected to the controller may be configured to detect a relative longitudinal state of the plurality of at least one sensed dielectric elastomer unit in the MASM and to provide feedback to the controller. The controller, which may be a PID controller, may be configured to control contraction or expansion of the plurality of dielectric elastomer units based upon the detected relative longitudinal state of the at least one sensed dielectric elastomer unit. In other embodiments, an electromyographic (EMG) signal processing interface may be connected to the controller and to one or more EMG sensors configured to detect electrical activity of a living muscle, and the controller may be configured to control contraction or expansion of the plurality of dielectric elastomer units based upon a signal from the EMG signal processing interface.

Another aspect of the invention comprises a powered exoskeleton configured to be worn by a user, comprising one or more modular MASM actuators as described above. The powered exoskeleton comprises a frame including at least a proximal portion configured to be removably attached to the user proximal a joint of the user, and a distal portion configured to be removably attached to the user distal of the joint of the user. The proximal and distal portions configured to move relative to one another with at least one degree of freedom. Each MASM actuator proximal anchoring member is attached to the proximal portion of the frame at the proximal anchor point. Each MASM actuator tension member distal end is attached to the distal portion of the frame at the distal anchor point. Each tension member has an adjustable length between the proximal anchor point and the distal anchor point. The displacement of the respective tension member caused by contraction or expansion of each MASM actuator causes corresponding displacement of the distal portion of the frame relative to the proximal portion of the frame.

One or more tension members in the exoskeleton system may be connected to a displacement magnification system that converts a first amount of displacement of the tension member into a greater amount of displacement of the distal portion of the frame relative to the proximal portion. In certain embodiments, the frame may be configured for removable attachment to a pediatric user.

In one embodiment, the frame is configured for placement about an elbow joint of the user, such as having a proximal portion configured to be anchored about a shoulder of the user and a distal portion comprising a cuff configured to be anchored to a forearm of the user. In another embodiment, the frame may be configured for placement about an ankle joint of the user.

The controller may comprise a control system including one or more feedback sensors and is configured to activate preset sequences of the plurality of MASM actuators in response to specific detected system state conditions. In an embodiment in which the frame is configured for placement about an ankle joint of the user, the system may include at least one plantarflexion MASM actuator configured to augment ankle plantarflexor muscle function and at least one dorsiflexion MASM actuator configured to augment ankle dorsiflexor muscle function. The system may further comprise at least one inversion MASM actuator configured to augment ankle inversion muscle function and at least one eversion MASM actuator configured to augment ankle eversion muscle function. The controller may include a control system including a sensor configured to detect different phases of ankle motion during a walking gait of the user and to activate preset sequences of the plantarflexion, dorsiflexion, inversion, and eversion MASM actuators in synchrony with the detected phases of the walking gait. The sensor configured to detect different phases of ankle motion during the walking gait may comprise a gyroscope configured to detect bilateral shank angular velocity of the user for determining gait phase transitions and a plurality of stimulators for activating the MASM actuators.

In one embodiment, the powered exoskeleton is configured to rehabilitate a gait of a pediatric user with cerebral palsy, and the controller is configured with an algorithm for detecting gait phase based upon z axis bilateral shank angular velocity or a sum of bilateral shank angular velocity about three axes and which includes detection criteria tailored to gait phase transitions of children with cerebral palsy. The detection criteria tailored to gait phase transitions of children with cerebral palsy may include a delay in Initial Swing (ISw) detection until after a predetermined percentage of elapsed gait cycle, a delay in Mid-Swing (MSw) detection until a predetermined number of samples after ISw, a peak detection threshold for ISw set to a predetermined percentage of a smallest detected peak in a predetermined number of previous cycles, and a peak detection threshold for Terminal Swing (TSw) set to a predetermined percentage of a smallest detected valley in a predetermined number of previous cycles, wherein the peak for ISw may be evaluated as a sum of the bilateral shank angular velocity about the three axes, if desired for better resolution of the peak.

In one ankle embodiment, the distal portion of the frame may comprise a footplate configured for positioning beneath a foot of the user. The proximal portion of the frame may be configured for positioning about a lower leg of the user and further comprises an exoskeletal connector connecting the footplate to a connection point on the proximal portion of the frame, and configured to extend along the lower leg of the user. The plurality of dielectric elastomer units of each MASM actuator are disposed in a pocket that is attached to a textile member and configured to be removably anchored to the proximal portion of the frame. Each respective tension member may be confined for some portion of its length within a relatively low friction conduit in the textile member. The proximal portion of the frame may comprise a first portion configured to be mounted proximal of a knee of the user, a second portion configured to be mounted distal of the knee of the user, the first and second portions connected to one another on opposite sides of the knee of the user with opposite exoskeletal knee joints. The tension member connected to a dorsiflexion MASM actuator configured to augment ankle dorsiflexor muscle function may connect to a housing mounted to an adjustable, cable-reinforced instep strap connected to opposite sides of the footplate.

In certain ankle embodiments, the footplate may have a joint positioned to align with a metatarsal joint of the user's foot. The footplate joint may comprise one or more dielectric elastomer units connected to the controller, with the controller configured to modulate stiffness of the footplate joint by modulating power to the one or more dielectric elastomer units. The controller may further comprise a control system including a sensor configured to detect different phases of ankle motion during a walking gait of the user and to modulate stiffness of the footplate joint based upon detected phase of gait.

In embodiments with an exoskeletal connector connecting the footplate to a proximal portion of the frame and extending along the lower leg of the user, the exoskeletal connector may be configured for detachment and reattachment to the footplate. In some embodiments, the exoskeletal connector may have an adjustable stiffness. The exoskeletal connector may include one or more integrated dielectric elastomer units connected to the controller, in which case the controller is configured to modulate stiffness of the exoskeletal connector by modulating power to the one or more integrated dielectric elastomer units. The powered exoskeleton may have a control system including a sensor configured to detect different phases of ankle motion during a walking gait of the user, in which case the controller may be configured to modulate stiffness of the exoskeletal connector based upon detected phase of gait.

Another aspect of the invention comprises an ankle-foot orthosis (AFO) comprising a frame comprising at least a proximal frame portion configured to be removably attached to a user proximal an ankle joint of the user. The proximal frame portion connected to a footplate configured to be secured beneath a foot of a user. The footplate has a joint positioned to align with a metatarsal joint of the user's foot. The joint comprises one or more dielectric elastomer units proximally anchored to a proximal portion of the footplate and distally anchored to a distal portion of the footplate. The joint is connected to a controller configured modulate stiffness of the one or more dielectric elastomer units by modulating power to the one or more integrated dielectric elastomer units.

Yet another aspect of the invention comprises an exoskeleton comprising a frame, wherein at least one member of the frame has variable stiffness provided by at least one dielectric elastomer unit.

BRIEF DESCRIPTION OF THE DRAWINGS

FIG. 15B-1 schematically illustrates a front-left perspective view of the second exemplary ankle exoskeleton embodiment.

FIG. 15B-2 schematically illustrates a highlighted portion of FIG. 15B-1, showing a longitudinal section of an exemplary conduit in textile member 1520 having an exemplary tension member inside.

FIG. 15C schematically illustrates a right side of the second exemplary ankle exoskeleton embodiment.

FIG. 15D schematically illustrates a right-rear perspective view of the second exemplary ankle exoskeleton embodiment.

DETAILED DESCRIPTION OF THE INVENTION

Aspects of the invention comprise the use of modular artificial skeletal muscle (MASM) actuators as described herein, each of which comprises a plurality of dielectric elastomer actuator (DEA) units assembled in series or in parallel. While the examples as presented herein use stacked DEA, specifically stacked DEA made by CTsystems (CT25.0-15-15-71, Compliant Transducer Systems, Dubendorf, Switzerland), depicted in FIG. 2, referred to specifically herein as CT-SDEA, the invention is not limited to any particular configuration of DEA (e.g. stacked, folded, etc.), nor is it limited to any particular manufacturer. Thus, even when referred to as CT-SDEA in various places herein, it should be understood that the other types of DEA muscle may also be applicable to any of the embodiments as discussed herein. Unless expressly indicated, use of DEA or SDEA or CT-SDEA should herein should not be interpreted as a limitation.

Figure 2:
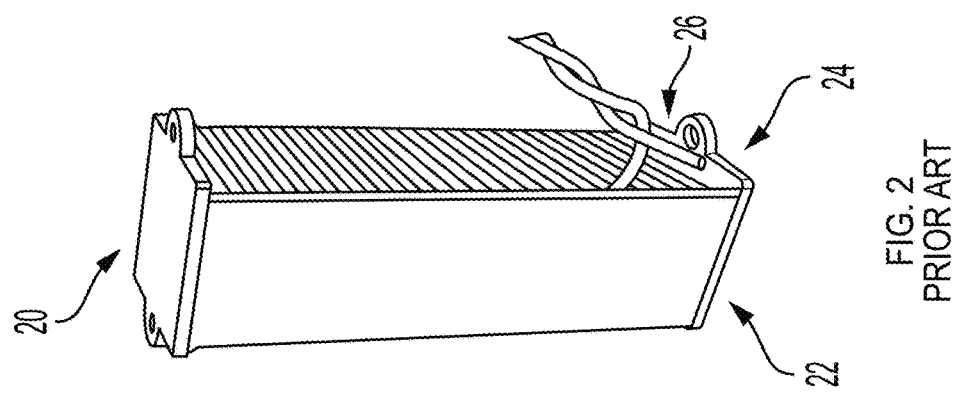
FIG. 2 illustrates an exemplary CT-DEA unit.
Figure 1:
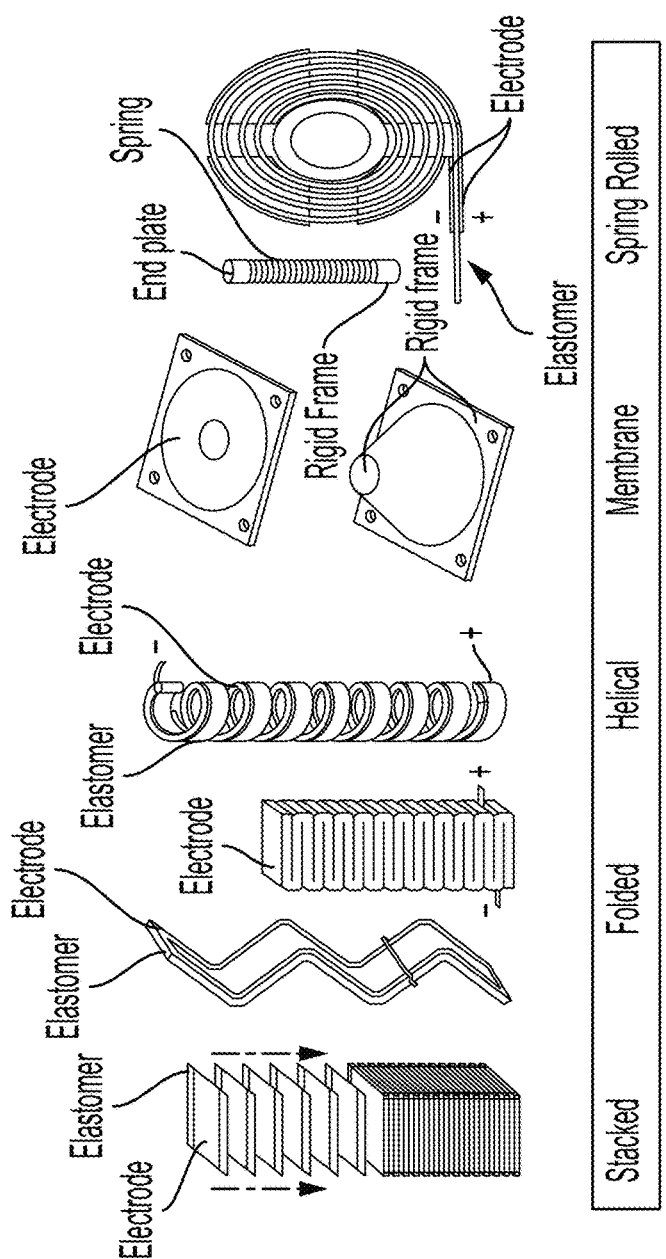
FIG. 1 illustrates various types of known DEA structures.
Figure 3B:
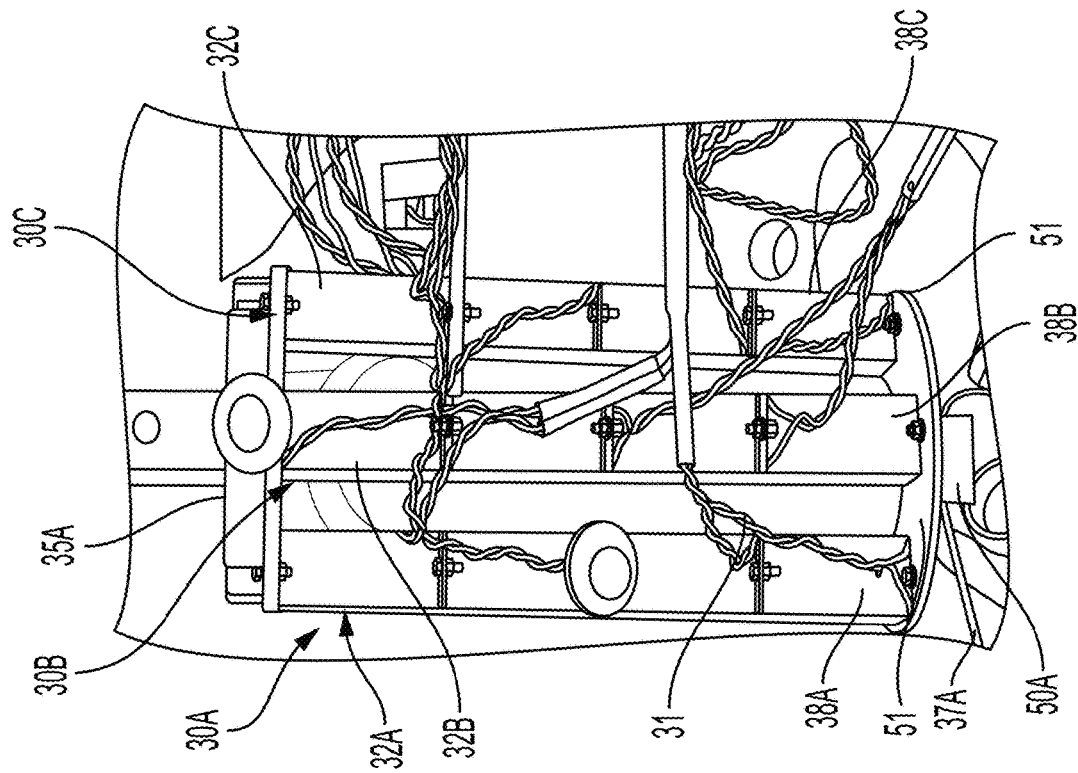
FIG. 3B illustrates an exemplary 3×4 modular artificial skeletal muscle (MASM) actuator.
Figure 3A:
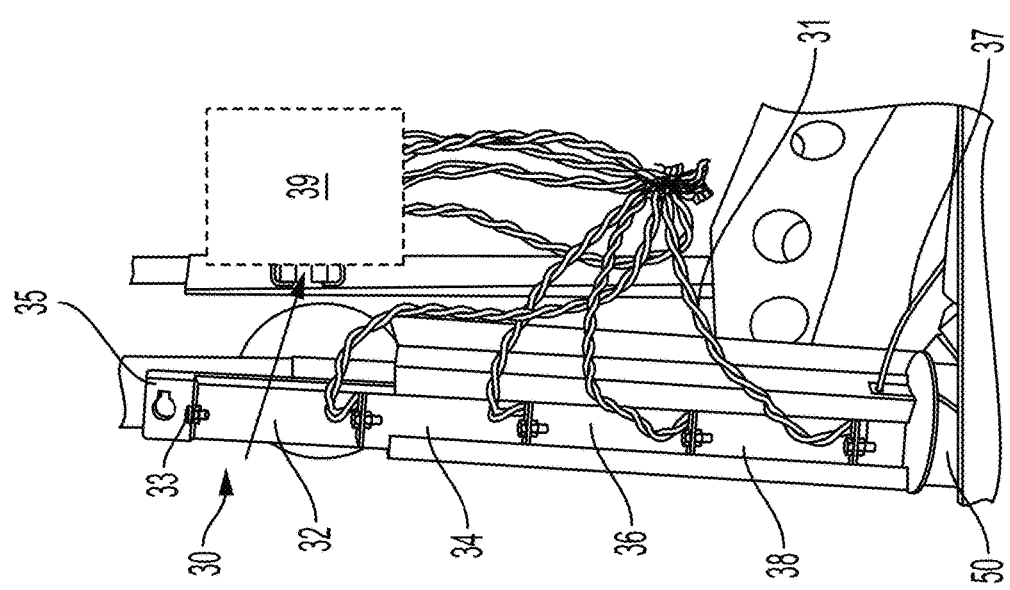
FIG. 3A illustrates an exemplary 1×4 modular artificial skeletal muscle (MASM) actuator.

As shown in FIG. 2, each CT-SDEA unit has opposite endplates 20, 22 and connection points 24, 26 for positive and negative terminals connected to a power supply (not shown). Exemplary MASM actuators comprise a plurality of DEA units assembled in series (FIG. 3A) and/or in parallel (FIG. 3B). FIGS. 3A and 3C depict a 1×4 (one set 30 of four DEA units 32, 34, 36, 38 in series) assembly and FIG. 3B depicts a 3×4 (three parallel sets 30A, 30B, 30C of four DEA units in series) assembly. Each DEA unit is ultimately connected to a controller 39 (schematically depicted in FIG. 3A, but omitted in FIG. 3B, to reduce clutter) via one or more electrical connectors 31.

In MASM actuator 30, DEA unit 32 is a proximal DEA unit and DEA unit 38 is a distal DEA unit. In use, the proximal DEA unit is anchored to a proximal anchor point relative to the user, which may be a frame in an exoskeleton application, wherein the frame is removably affixed to a patient. The anchoring to the frame may comprise, for example, the end plate of the DEA unit being affixed (e.g. with a fastener 33, such as a nut 33B and bolt 33A as depicted in FIG. 3C) to a proximal connector 35, which connector may be a single member or an assembly of components, and may be configured to be removably attached to the frame or other element relative to the patient. In the MASM actuators 30A, 30B, 30C, each of the three sets of four DEA units arranged in parallel has a proximal DEA unit 32A, 32B, 32C that connected to connector 35A.

Different configurations of the artificial skeletal muscle show linear additive behavior of force and displacement when the DEAs are configured in parallel and in series. When DEAs are added in parallel, the maximum force generated is multiplied by the number of actuators used (contraction displacement remains the same), while when added in series, contraction displacement is multiplied by the number of actuators used (force generation remains the same). For example, adding CT-SDEA units in series (e.g. 1×1 to 1×5) shows constant force generation at ~10 N of maximum force. Configurations with two CT-SDEA units in parallel (2×1 and 2×2) and three CT-SDEA units in parallel (3×1 and 3×4) showed ~20 N and ~30 N of maximum force respectively. Increasing the number of CT-SDEA units increases the MASM assembly's maximum shortening almost linearly. For example, under 40 g of tensile load, a single CT-SDEA unit showed 1.3 mm of maximum shortening and an assembly of five CT-SDEA units in series showed 6.53 mm (i.e., 5×1.3). This linearity may decrease with increasing tensile load.

As depicted in FIG. 3A, the distal DEA unit 38 is connected to a proximal end of a tension member 37. Tension member may comprise a flexible, non-extendable cable, such as a wire cable. The tension member may be a tension-only cable, such as a traditional cable, or a push-pull cable, which may offer the advantage of reducing slack in the cable and more affirmatively creating the desired displacement when the MASM expands. The tension member is not limited to any particular type of member or materials of construction; however, the non-extensibility of the cable is relatively important so that any displacement of the artificial muscle is transmitted to the desired endpoint with minimal loss. The connection between the distal DEA unit 38 and the tension member 37A is preferably via a distal connector or connector assembly 50 that provides an adjustable connection that permits adjustment of the length of the tension member. Likewise, as depicted in FIG. 3B, all three distal DEA units 38A, 38B, 38C are connected to common distal plate 51 that is connected to connector 50A, and the proximal end of tension member 37A is connected to connector 50A, preferably by an adjustable connection.

Figure 3D:
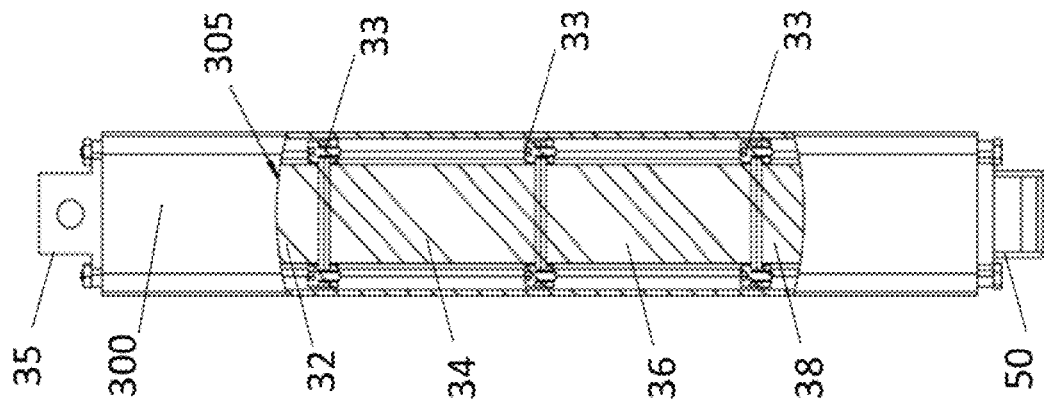
FIG. 3D illustrates the exemplary 1×4 MASM actuator of FIG. 3C, encased in a flexible, electrically insulating, minimal friction covering.
Figure 3C:
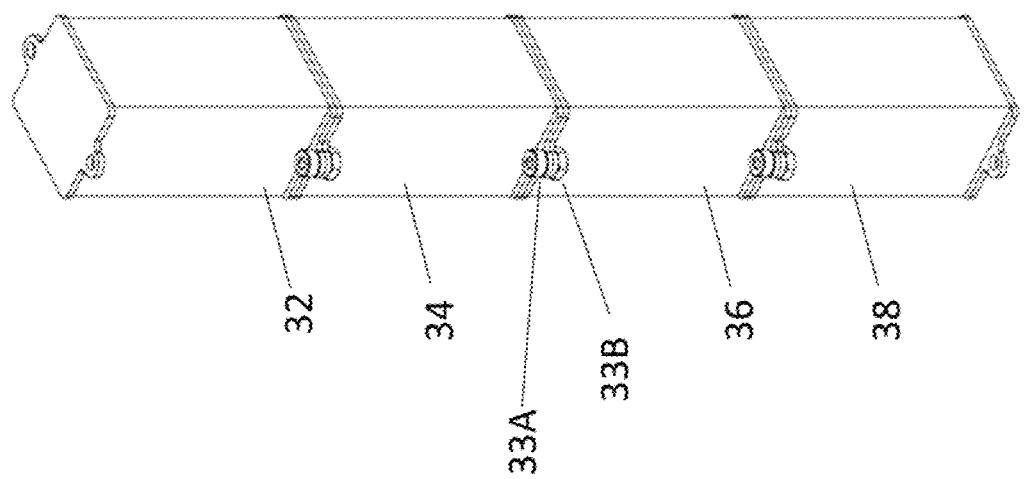
FIG. 3C depicts an isolated view of the exemplary 1×4 MASM actuator of FIG. 3A.

In preferred embodiments, the artificial muscle assembly may preferably be confined in a low-friction, flexible, electrically insulating covering 300, as shown in FIG. 3D, such as comprising an elastic silicone film. In addition to facilitating movement with minimal friction, the electrically insulating covering provides protection against electrical shocks, as the artificial muscle may generate strong, painful sparks, if touched. Film 300 is depicted with a clear section 305 for illustrative purposes only, to enable visualization of the underlying CT-SDEA units 32, 34, 36, 38 and connecting fasteners 33 within the covering 300. The covering 300 preferably covers all of what would otherwise be exposed surfaces of the CT-SDEA units, and fully extends between proximal connector 35 and distal connector assembly 50. FIG. 3C depicts the CT-SDEA units and connectors without the covering.

Figure 5:
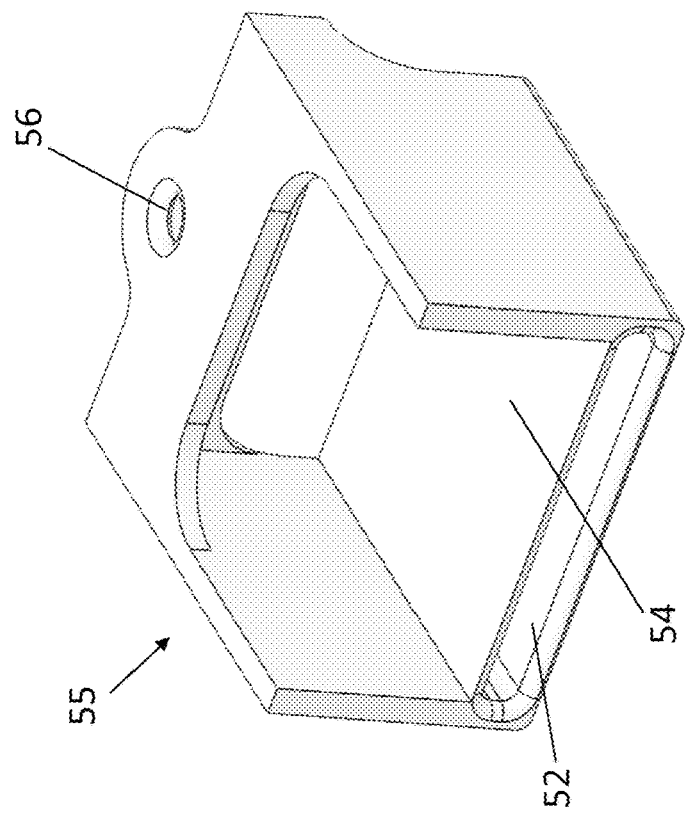
FIG. 5 illustrates an exemplary clamping unit housing.
Figure 4:
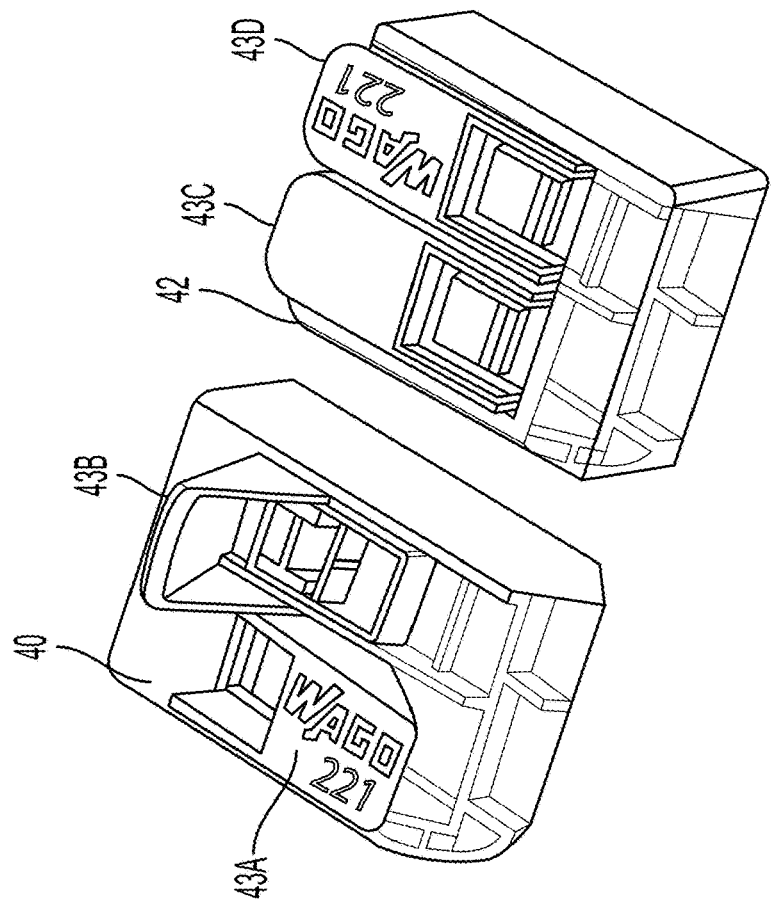
FIG. 4 illustrates a plurality of exemplary clamping units.

Exemplary components of a connector assembly are depicted in FIGS. 4 and 5. Clamping units 40, 42 shown in FIG. 4. Each clamping unit 40, 42 comprises a pair of wire clamps 43A, 43B and 43C, 43D, respectively. Clamps 43A, 43C and 43D are depicted in a closed position, whereas clamp 43B is depicted in an open position. Clamps may be disposed in a housing such as housing 55, shown in FIG. 5. While housing 55 has certain features tailored to a specific application, as discussed in detail herein later, it is representative of exemplary housings is sized to receive the clamping units permanently affixed thereto, and has features for anchoring the housing to a frame or the like. In one embodiment, the wire clamp is placed in the open positon, the proximal end of the tension member is threaded into the clamp as far as desired to give the tension member a desired length, and the clamp is closed. This permits adjustability of the length of the tension member to tailor the MASM assembly to a particular patient.

Figures 14A, 14B:
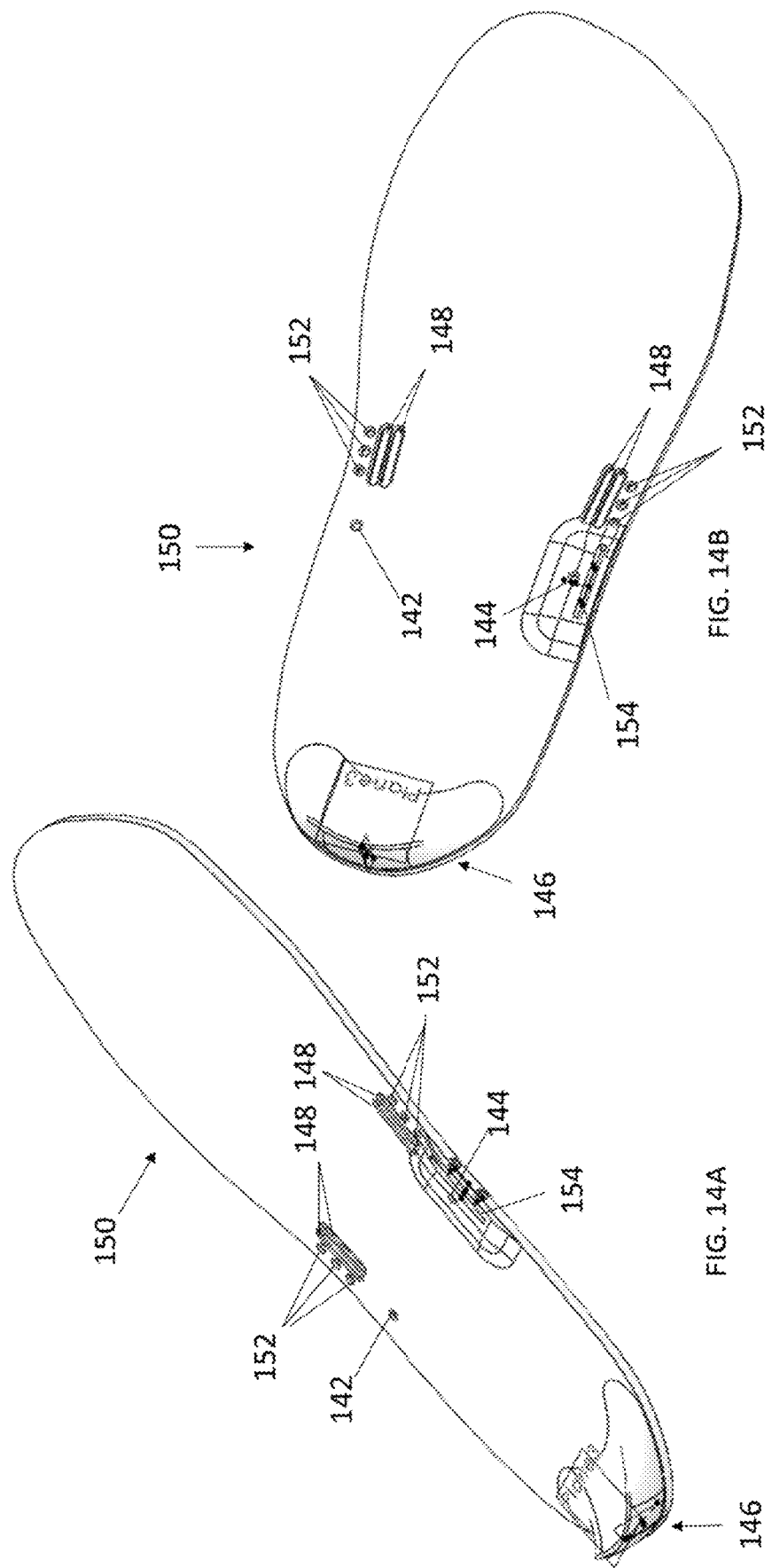
FIGS. 14A and 14B schematically illustrate an exemplary footplate.

The distal end of the tension member 37 is typically affixed to a distal anchoring point, such as to a footplate 150 as depicted in FIGS. 14A and 14B, and discussed in detail herein later. The distal end may be affixed with a non-adjustable connection, with the proximal connection providing ample modularity and adjustability, or the distal end may be also affixed with an adjustable connection. In some embodiments, the tension member 37 may form a loop in which both free ends are proximal ends that connect to the proximal anchoring point (e.g., one each in clamps 43A and 43B, and the distal end of the tension member is the distalmost point of the loop, where that loop connects to the distal anchor point.

With the MASM actuators thus anchored at their proximal end and connected at their distal end to a distal anchoring point via a tension member, the controller, which is attached to a power source and to the plurality of dielectric elastomer units, applies a voltage to the plurality of dielectric elastomer units in each MASM assembly simultaneously, thus causing contraction or expansion of plurality of dielectric elastomer units, which contraction or expansion causes displacement of the tension member.

Electronics

A high voltage (HV) amplifier (such as, but not limited to, an RC250-1.5P, Matsusada Precision Inc., Shiga, Japan, with 1500 V and 165 mA maximum output voltage and current respectively) may be used for providing driving voltage in a range of 0-1230 V for the CT-SDEAs. FIG. 6A depicts the electrical circuitry of the HV amplifier, VDC, discharge resistance, $R_{dts}$, and CT-SDEA. Although depicted as a CT-SDEA, similar circuitry may be applicable to other types of DEA as well. The DEA may be modeled as a parallel variable capacitor, C, and resistor, R, in series with two electrode resistors, $R_E$. The combination of $R_E$ and R model the non-ideal leakage current through the dielectric. Variability in the C, R, and $R_E$ is due to length modulation of the DEA, and consequently, changes in the electrical characteristics of the compliant capacitor. Electrode resistance of each of the CT-SDEA's layers has been reported at 50 kΩ. Considering 1600 parallel layers of DE material in each CT-SDEA unit, the total electrode resistance may be as small as 31.25Ω in a resting state. A discharge resistor $R_{dis}$ (e.g. 1 MΩ) may be connected in parallel to increase the rate of discharging the SDEA, and thereby, increase the pace of recovery, i.e., returning to initial state.

To charge the CT-SDEA for full contraction, the transient current consumption of one actuator may reach as high as 22.77 mA for a couple of milliseconds. For safety concerns, current may be limited by connecting a resistor in-series with the actuator, which also limits the contraction velocity.

In active exoskeletons, where assisting motion is usually the main goal, the shortening, i.e., longitudinal displacement, of the artificial skeletal muscle is designed to be large enough to allow for its contraction alongside the impaired muscle. Because the maximum strain of the DEAs is substantially lower than skeletal muscle, it may be advantageous to leverage the substantial force of the SDEAs and magnify the displacement using a mechanical linkage, or to assist the user's skeletal muscle contraction only in a portion of the user's range of motion (RoM).

Self-Sensing

Unlike conventional actuators, DEA units do not require an independent sensing device such as encoder or tachometer. Changes in DEA unit electrical characteristic may be used to infer length modulation. When multiple degrees of freedom are needed, in applications such as rehabilitation robotics, this feature may substantially reduce the cost, efficiency and complexity of the system.

Figure 8:
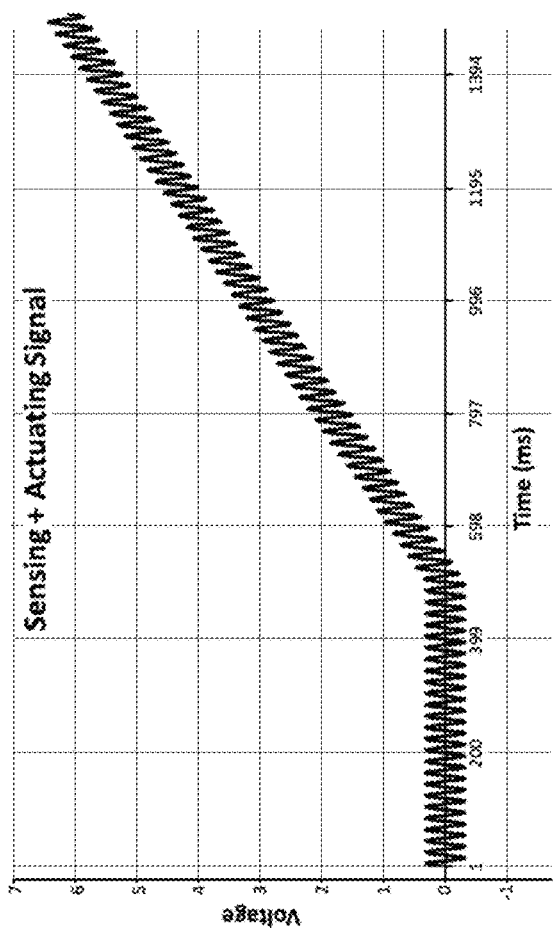
FIG. 8 illustrates an exemplary sensing+actuating signal curve relevant to self-sensing applications.
Figure 9:
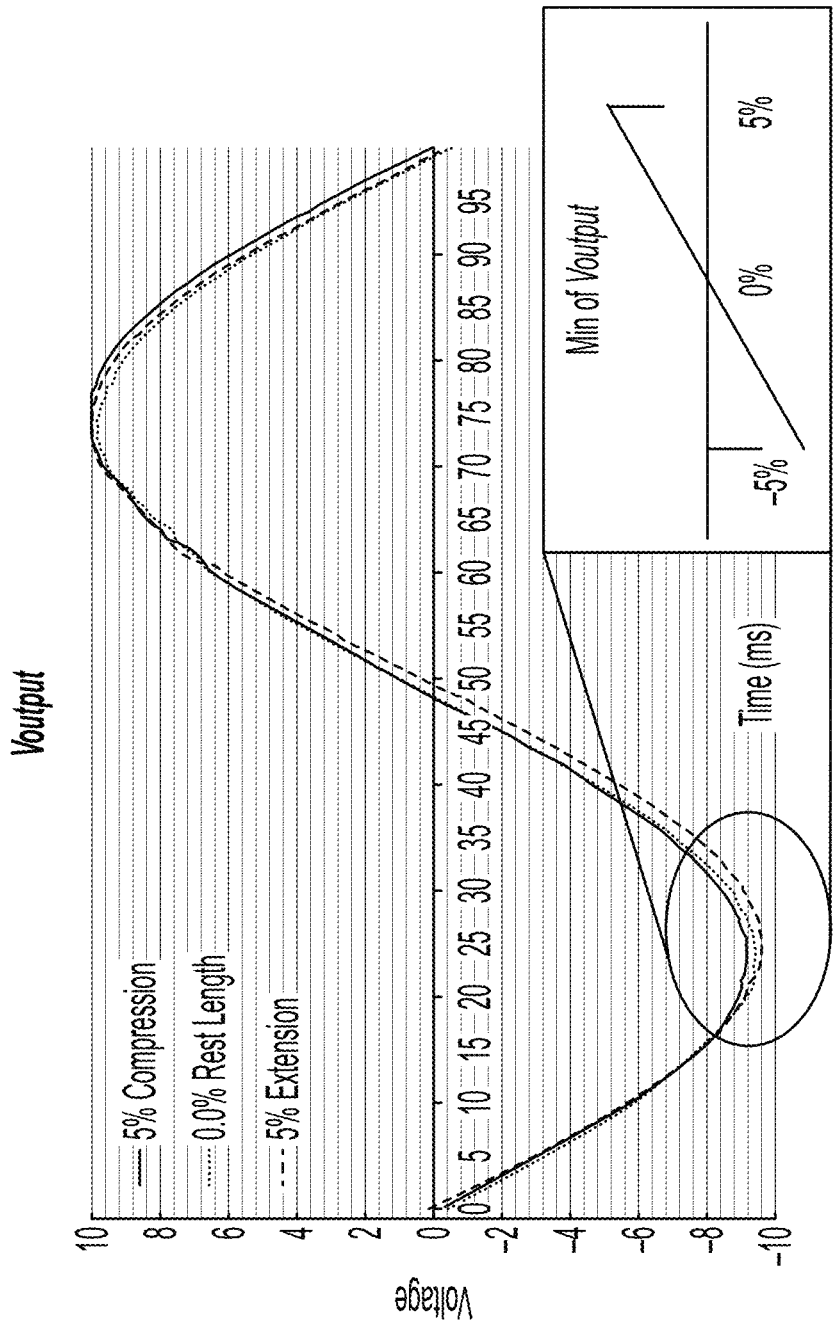
FIG. 9 illustrates exemplary curves relevant to self-sensing applications.
Figure 10:
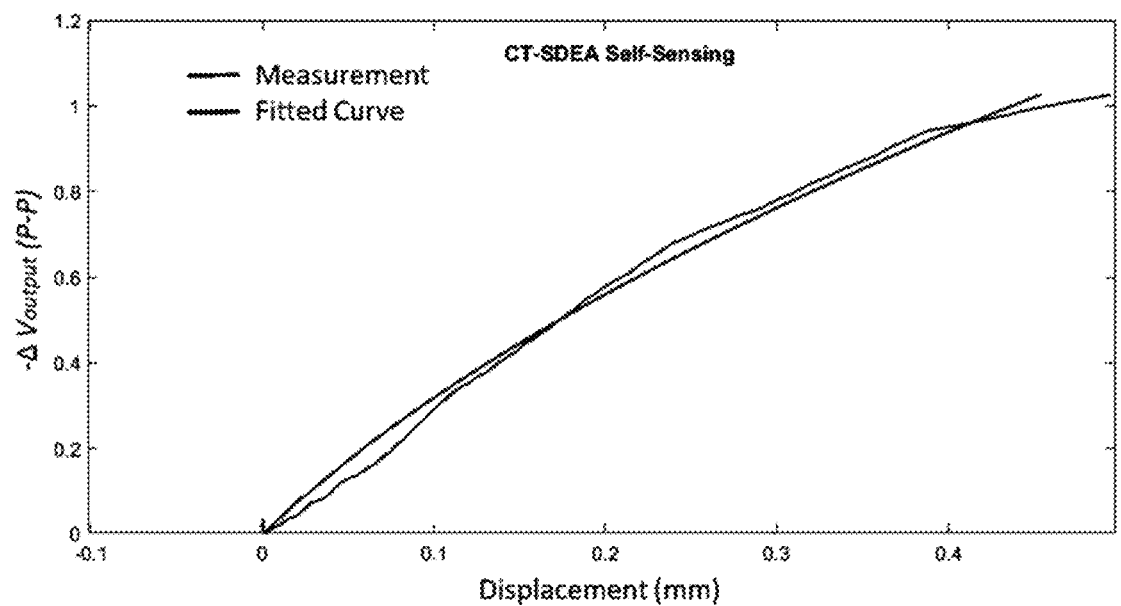
FIG. 10 schematically illustrates measured and fitted curves relevant to a self-sensing application.

Sensor-free closed-loop control of a DEA unit or assembly of a plurality of DEA units is attainable using a self-sensing length modulation system that mimics the proprioception in human motor control. During actuation, the changes in the electrical characteristics of the DEA, as a compliant capacitor, are used for sensing the longitudinal contraction of the actuator. Self-sensing may be effected by using a low-pass filter designed by connecting a resistor in series with the DEA, then superimposing a high frequency signal to the driving, low frequency, activation waveform, such as is depicted in FIG. 8. Measuring the amplitude of the output of the low-pass filter permits displacement of the DEA to be inferred. For example, changes in the amplitude of the 10 Hz sinusoid signal at resting length (0%), 5% compression, and 5% extension, are depicted in FIG. 9. As the DEA is compressed, the amplitude of the sensing signal decreases, and as it extends, the signal's amplitude increases. The self-sensing information is then fitted to actual displacement information to establish the relationship between self-sensed length and actual displacement or degrees of joint rotation. Real-time length self-sensing of the CT-SDEA in one embodiment positioned relative to displacement sensor data is depicted in FIG. 10. The self-sensing data may be derived from the changes in the peak-to-peak (P-P) value of $V_{output}$ (as depicted in FIG. 10, the self-sensing data shown as a negative, to follow the trend of the output laser displacement sensor). The equation of the fitted curve depicted in FIG. 10 for the exemplary CT-SDEA was found to be.

$$0.1827x^2 + 0.2543x + 0.000425$$

It should be understood, however, that the invention is not limited to any particular correlation between the self-sensed data and actual displacement. Importantly, the self-sending data corresponding to a particular arrangement of DEA units may be mapped to a curve that permits use of a single self-sensing relationship for a single measured DEA unit that can be mapped to the MASM as a whole (comprising, e.g., 1×4, 3×5 DEA units), rather than sensing information for each separate DEA in the stack or for the stack as a whole.

Figure 11:
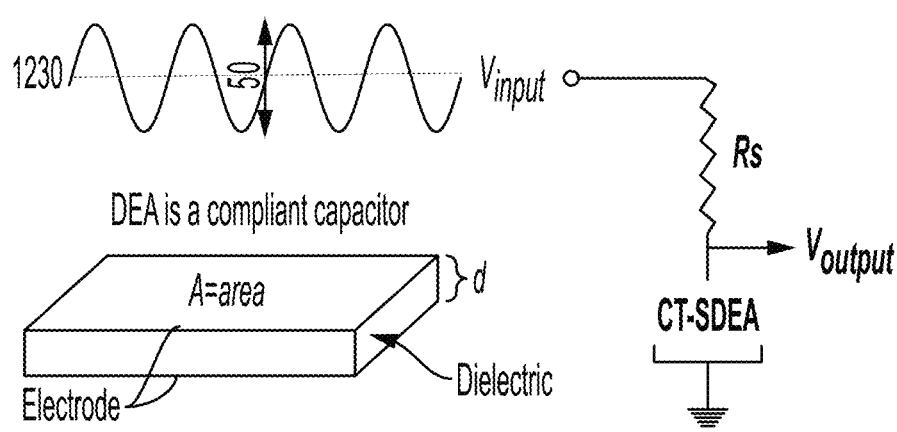
FIG. 11 schematically illustrates functional and electrical representations for an exemplary DEA actuator.

Many self-sensing techniques are known and have been documented, and the invention is not limited to any particular self-sensing technique. However, the exemplary DEA self-sensing mechanism as described above is now described in more detail, without limitation thereto. This DEA self-sensing mechanism works by inferring longitudinal contraction information from changes in the electrical characteristics of the DEA as illustrated in FIG. 11. The impedance of the DEA ($X_c$) changes by its longitudinal contraction, which can measure by recording $V_{output}$, using Equation 1. DAE's impedance ($X_c$) is inversely proportional to the DEA's capacitance, C. By using Equation 2, and the known frequency of $V_{input}$, f, C can be measured. Finally, using Equation 3, the thickness of the DEA (d) can be calculated.

$$V_{output} = \frac{X_c}{R + X_c} V_{input} \quad (1)$$

$$X_c = \frac{1}{2\pi f C} \quad (2)$$

$$C = \varepsilon_0 \varepsilon_r \frac{A}{d} \quad (3)$$

As the DEA as depicted in FIG. 11 contracts longitudinally, i.e., d decreases, its capacitance increases (per Equation 3); consequently, in the frequency domain, the cut-off frequency, $F_c$ decreases (per Equation 4):

$$F_c = \frac{1}{2\pi RC} \quad (4)$$

where R is the total resistor in the electrical circuitry including $R_s$.

Figure 7:
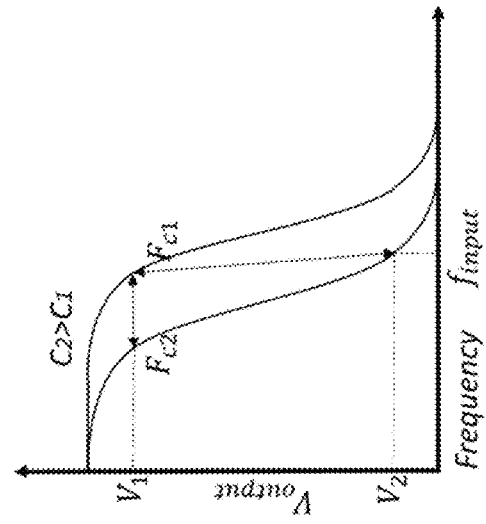
FIG. 7 illustrates the parts of an exemplary set of curves relevant to self-sensing applications.

In other words, when a DEA longitudinally contracts its capacitance increases, thus the $F_c$ decreases, consequently, the attenuation of input signal increases, which results in $V_{output}$ decrease, as depicted in FIG. 7.

Figure 6B:
FIG. 6B illustrates an exemplary simplified circuit used for modeling DEA behavior.
Figure 6A:
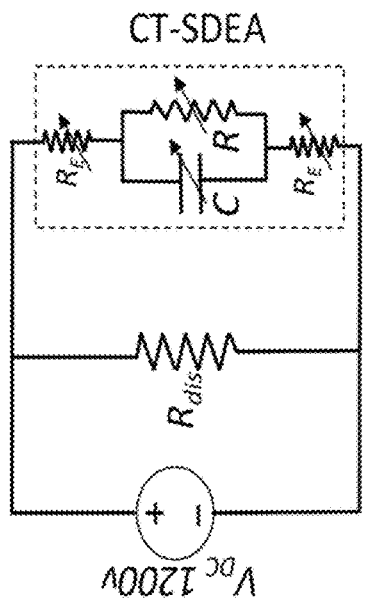
FIG. 6A illustrates an exemplary electrical circuit comprising a DEA.

The electrical model of a DEA depicted in FIG. 6A, in which $C_p$ and $R_p$, are its variable capacitor and resistor, respectively, can be simplified to the model shown in FIG. 6B, because the variability in Cp, R, and $R_E$ are due to the length modulation of the CT-SDEA, but in the low frequency range (e.g., 10-100 Hz), $R_E$ can be neglected.

Using Laplace transformation, the impedance of the CT-SDEA can be calculated using Equation 5.

$$X_c = \frac{R_p}{1 + R_p C_p s} \quad (5)$$

By adding Equation 5 to Equation 1, the $V_{output}$ to $V_{input}$ transfer function can be derived (Equation 6), which is a first order lag system, high pass filter.

$$H(s) = \frac{R_p}{R_s R_p C_p s + R_{p+R_s}} \quad (6)$$

For a stacked DEA, $C_p$ and $R_p$ can be calculated using the slightly modified formulas Equations 7 and 8, respectively. Where n is the number of stacked layers in the CT-SDEA; $A_e$ is the active area of each layer (the area covered by electrode); $d_0$ is the resting length of the actuator excluding the thickness of its end plates; $\varepsilon_r$ and $\varepsilon_0$ are relative permittivity and void permittivity respectively of the polymer (silicon rubber for CT-SDEA); V is activation voltage; and d is length of the activated actuator.

$$C_p(d) = n^2 \varepsilon_0 \varepsilon_r \frac{A_e}{d0}\left(\frac{d0}{d}\right)^2 \text{ or } C_p(d) = C_{p0}\left(\frac{d0}{d}\right)^2 \quad (7)$$

$$R_p(d) = \frac{1}{n^2}\rho_0 \frac{d0}{A_e}\left(\frac{d}{d0}\right)^2 \text{ or } R_p(d) = R_{p0}\left(\frac{d}{d0}\right)^2 \quad (8)$$

Using Equations 6 and 7, the polymer's time constant $\tau_p$, can be calculated. Equation 9 shows that the actuator's time constant only depends on the polymer's physical characteristics:

$$\tau_p = C_p R_p = \varepsilon_0 \varepsilon_r \rho_0 \quad (9)$$

In Equation 9, is the resistivity of the dielectric material, i.e., silicon rubber in CT-SDEA.

Table I provides definitions for $R_p$ and $C_p$ parameters and exemplary measured or reported values.

TABLE I

| Parameter | Detention | Value |
|---|---|---|
| $d_0$ | Resting length of the CT-SDEA | 36.89 mm |
| $A_e$ | Active are of the CT-SDEA | 134.56 × 10⁻⁶ m |
| n | Number of layers | 1600 |
| $C_{p0}$ | CT-SDEA's capacitance at resting length | 237 × 10⁻⁹ F |
| $\in_r$ | Silicon rubber relative permittivity | 2.8 |
| $\in_0$ | Void permittivity | 8.854187187 × 10⁻¹² |
| $R_{p0}$ | CT-SDEA's resistance at resting length | 191 × 10⁵ Ω |
| $\rho_0$ | Dielectric resistivity | 1.8264 × 10¹¹ |

The values for $R_{p0}$ and $\rho_0$ may be calculated empirically. During an isometric contraction, the length of the CT-SDEAs was held constant at a rest length under no compression or extension. After application of a square activation waveform activation, with amplitude of 1230 V and period of 5 s, the CT-SDEAs showed 38 ms time constant, during the discharge period. Using Equation 8 and considering a 1 MΩ discharge resistance connected in parallel with the CT-SDEA, $R_{p0}$ and $\rho_0$ were calculated at 191×10⁵Ω and 1.8264×10¹¹, respectively.

The gain of a first order lag system, in time domain, K (Equation 10), for a sinusoidal input with frequency of f, is presented in Equation 11. This gain may be calculated for different Rs and input frequencies as the length of the CT-SDEA changes. The time constant, τ and A in H(s) (Equation 6) is shown in Equation 12 and 13, respectively.

$$\frac{A}{\tau s + 1} \quad (10)$$

$$K = \frac{A}{\sqrt{(1+(2\pi f\tau)^2)}} \quad (11)$$

$$\tau = \frac{R_s \varepsilon_r \varepsilon_0 \rho_0 d_0^2}{R_s d_0^2 + R_0 d^2} \quad (12)$$

$$A = \frac{R_0 d^2}{R_s d_0^2 + R_0 d^2} \quad (13)$$

Self-sensing circuits may be connected to the controller for the MASM to provide feedback to the controller, and the controller may thus be configured to control contraction or expansion of each MASM assembly of DEA units based upon the detected longitudinal state. Use of such self-sensing may permit the controller to operate as a PID (proportional-integral-derivative) controller. In rehabilitation robotics, closed-loop controls (such as provided by a PID controller) are more preferable due to reliability. In such applications, precise displacement feedback may be an integral component of a robust closed-loop motion control.

EMG Control

In some embodiments, however, open-loop control of DEAs using biosignals, i.e., EMG, EEG, and ECG, for wearable technology may also be used. Thus, the MASM actuator may comprise an electromyographic (EMG) signal processing interface connected to the controller and to one or more EMG sensors configured to detect electrical activity of a living muscle, wherein the controller is configured to control contraction or expansion of the plurality of DEA units based upon a signal from the EMG signal processing interface. For example, FIG. 15C schematically illustrates a sensor 10 connected to a processor 12 connected to a controller 39, which general depiction may be relevant to multiple, different embodiments. With respect to an EMG-controlled embodiment, sensor 10 may comprise an EMG sensor, and processor 12 may comprise a signal processing interface connected to controller 39, with the controller configured to trigger MASM actuators (disposed in pockets 1580, 1590).

Exoskeletons

Figure 12B:
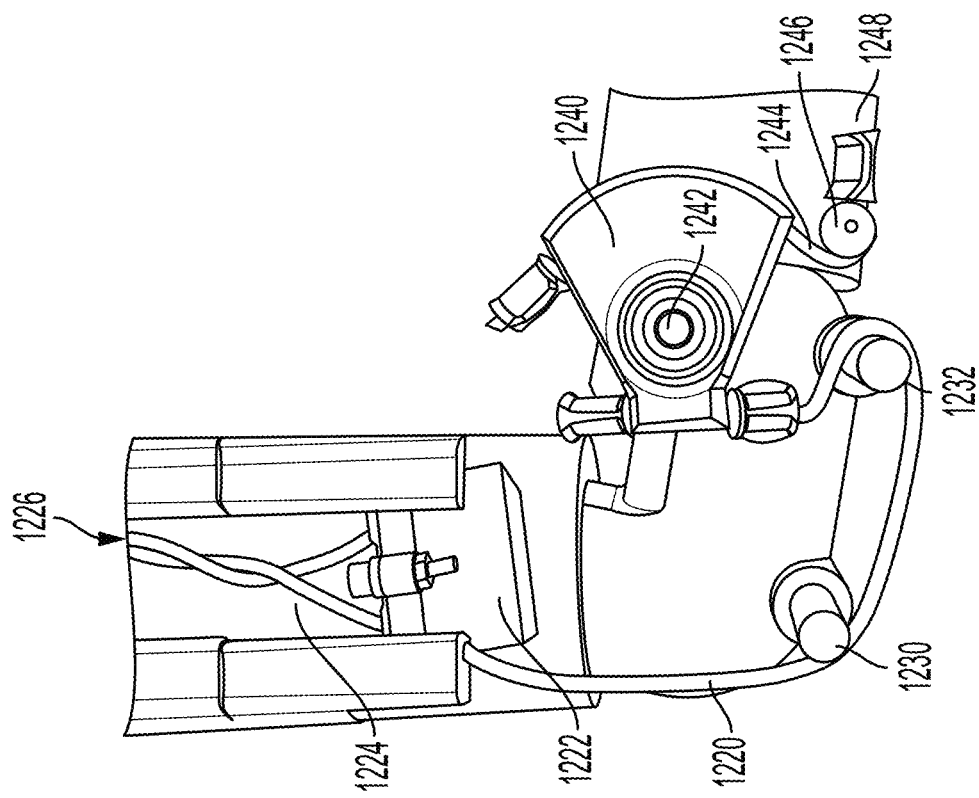
FIG. 12B schematically illustrates an exemplary displacement magnifier embodiment.
Figure 12A:
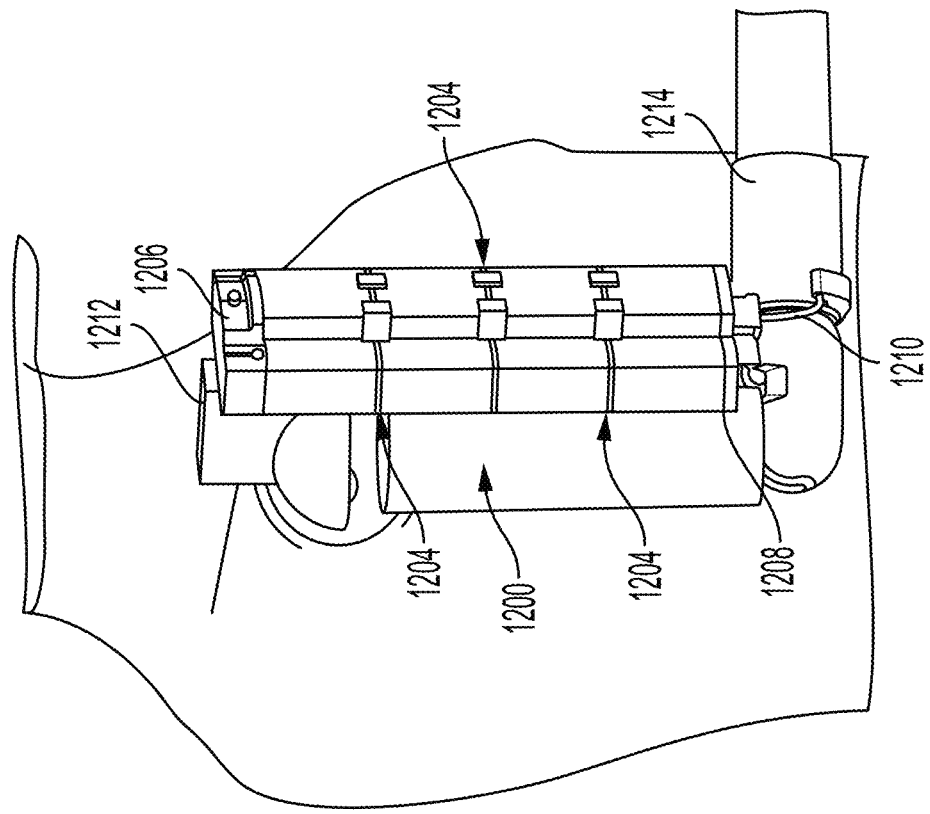
FIG. 12A schematically illustrates an exemplary elbow exoskeleton embodiment.

FIG. 12A depicts a CAD model of the schematic components of an exemplary exoskeleton 1200, powered by a 3×4 MASM 1202. The design contains three brackets located around the end plates of connecting CT-SDEA units to confine undesirable motion of the artificial muscle, and minimize any impact caused by bowing. The artificial muscle is preferably confined in a low friction, flexible, electrically insulating covering, as shown in FIG. 3D. To further restrict undesired motion, the artificial muscle assembly may be also be attached to a harder skeletal-like connecting frame, such as comprising top plate 1206 which connect the proximal CT-SDEA units to the proximal portion 1212 of the exoskeleton frame, and bottom plate 1208 connecting the distal CT-SDEA units to the tension member 1210, which is connected to a proximal end of distal portion 1214 of the exoskeleton frame. In the embodiment depicted in FIG. 12A, proximal portion 1212 of the frame is configured to be anchored about a shoulder of the user and the frame distal portion 1214 comprises a cuff configured to be anchored to a forearm of the user. The mechanisms for anchoring the frame to the user are only shown schematically, and it should be understood that the frame may have any geometry, including to provide a desired degree of rigidity for the proximal (shoulder) portion, additional components that, for example, are disposed across the user's body to the other side (e.g. across the rib cage, or to the other shoulder).

Adding a mechanical transmission, such as a mechanical linkage, for magnifying displacement may be highly desirable for some exoskeleton applications. An exemplary magnification system, for use in connection with an elbow exoskeleton, is depicted in FIG. 12B as a cam-shaped pulley system. As depicted, proximal end of tension member 1220 (e.g. wire cable) is adjustably affixed to connector housing 1222 attached to the distal CT-SDEA unit 1224 of MASM assembly 1226. Member 1220 extends around pulleys 1230, 1232 and connects to proximal side of cam 1240, which is rotatable about axial pin 1242. The distal side of cam 1240 is attached to another tension member 1244, which attaches to an anchor point 1246 on the distal portion 1248 of the exoskeleton frame. In this way, a first amount of displacement of the tension member 1220 is magnified by the foregoing system into a second amount of displacement of the distal portion of the frame relative to the proximal portion that is greater than the amount of displacement of tension member 1220. The invention is not limited to any particular type of magnification assembly.

Exemplary exoskeleton embodiments for use about an ankle joint of a user are depicted in FIGS. 13A-15D. Like the exoskeleton embodiment depicted in FIGS. 12A and 12B for use about an elbow joint of a user, each embodiment comprises a frame comprising at least an proximal portion configured to be removably attached to a user proximal a joint of the user and a distal portion configured to be removably attached to the user distal of the joint of the user, with the proximal and distal portions configured to move relative to one another with at least one degree of freedom. One or more modular MASM actuators, each anchored by an actuator proximal anchoring member attached to the proximal portion of the frame at the proximal anchor point, include a tension member having its distal end attached to the distal portion of the frame at a distal anchor point. Each tension member preferably has an adjustable length between the proximal anchor point and the distal anchor point. In all of the embodiments, displacement of the respective tension member caused by contraction or expansion of each MASM actuator causes corresponding displacement of the distal portion of the frame relative to the proximal portion of the frame.

As shown in the embodiment 1300 depicted in FIGS. 13A-13D, the proximal portion 1302 of the exoskeleton frame comprises a proximal cuff 1304 configured to be mounted proximal of a knee of the user and a distal cuff 1306 configured to be mounted distal of the knee of the user, with the proximal and distal portions connected to one another on opposite sides of the knee of the user with opposite exoskeletal knee joints 1308, 1310. The distal portion 1320 of the frame comprises a footplate configured for positioning beneath a foot of the user, such as the footplate depicted in FIGS. 14A and 14B. In some embodiments, the footplate may extend above the plantar aspect of the user's foot, and may even form a shape in the nature of a shoe. The depiction in FIGS. 13A-13D is intended only to be schematic, and tends to show connections directly to the shoe, but it should be understood that the connections may all terminate in a footplate similar to that shown in FIGS. 14A and 14B. The term "footplate," however, is not intended to refer only to the design shown in FIGS. 14A and 14B, and encompasses any distal portion configured with at least one component that extends beneath the user's foot, regardless of whether other elements may be present that extend above the sole of the user's foot.

The system includes ankle dorsiflexion MASM actuator 1330 configured to augment ankle dorsiflexor muscle function and ankle plantarflexion MASM actuator 1340 configured to augment ankle plantarflexor muscle function. An inversion MASM actuator 1350 is configured to augment ankle inversion muscle function (function that causes the sole of the foot to point in a medial direction) and an eversion MASM actuator 1360 configured to augment ankle eversion muscle function (function that is the opposite of inversion). Each of actuators 1330, 1360, and 1350 are depicted as 1×4 MASMs. Actuator 1340 is depicted as a 2×4 MASM. The invention is not limited to any particular configuration or number of units for each muscle, however, certain muscles may require more force in comparison to others, because of physiological needs. Because the plantarflexors create the necessary propulsion for walking, they typically generate more force in comparison to the other muscles around the ankle, and their artificial counterparts therefore also benefit from being able to generate proportionately relative forces. In fact, one advantage of the invention is the modular capability to tailor the muscle travel and force to the individual user. For example, a smaller or younger subject may not need the displacement of a 1×4 MASM (or may not have the physiological leg size to support the length of a 1×4 MASM), and may be able to use a 1×3 MASM in one or more locations. As that individual grows, he or she may need a larger unit, and an additional DEA unit may be added to the stack when needed (with all appropriate electrical and physical connections). Embodiments of the DEA units may be provided in any shape or size and with suitable connection interfaces to facilitate such modularized tailoring of the structures. The location of the connection point of the tension members to the distal portion of the exoskeleton (e.g. the footplate) may be adjusted based on the gait deviation and foot deformity of the user, which may be a highly useful feature because of the heterogeneity of cerebral palsy and ankle control dysfunction.

Figure 13B:
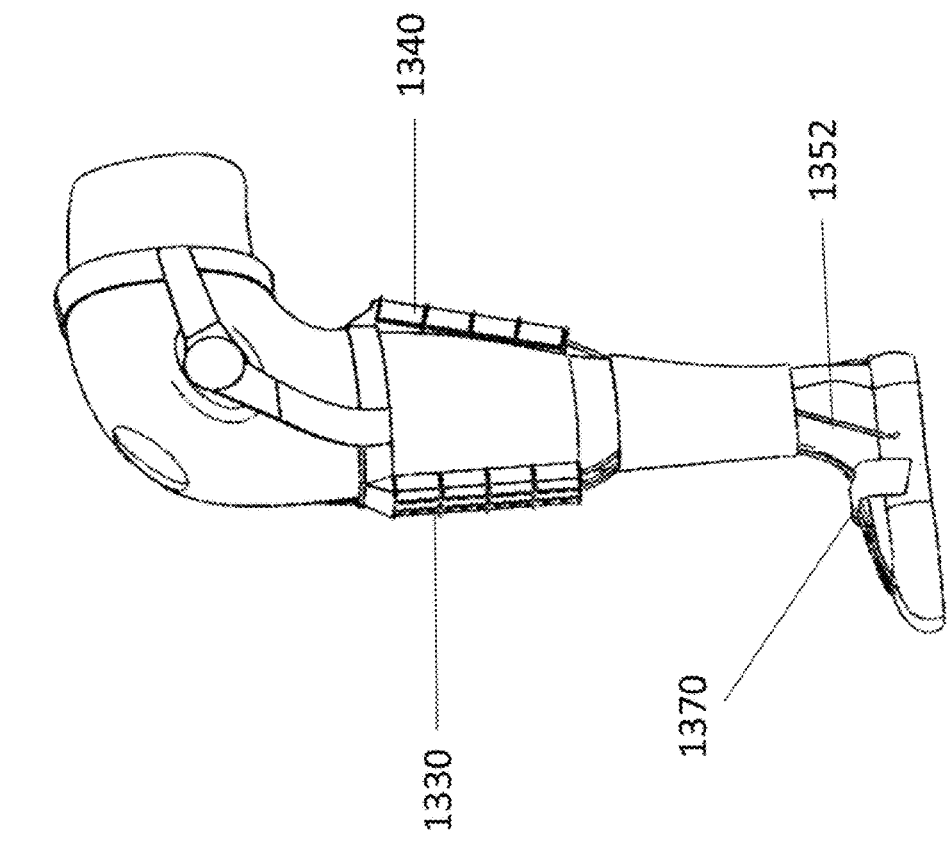
FIGS. 13A-13D schematically illustrate a first exemplary ankle exoskeleton embodiment.
Figure 13A:
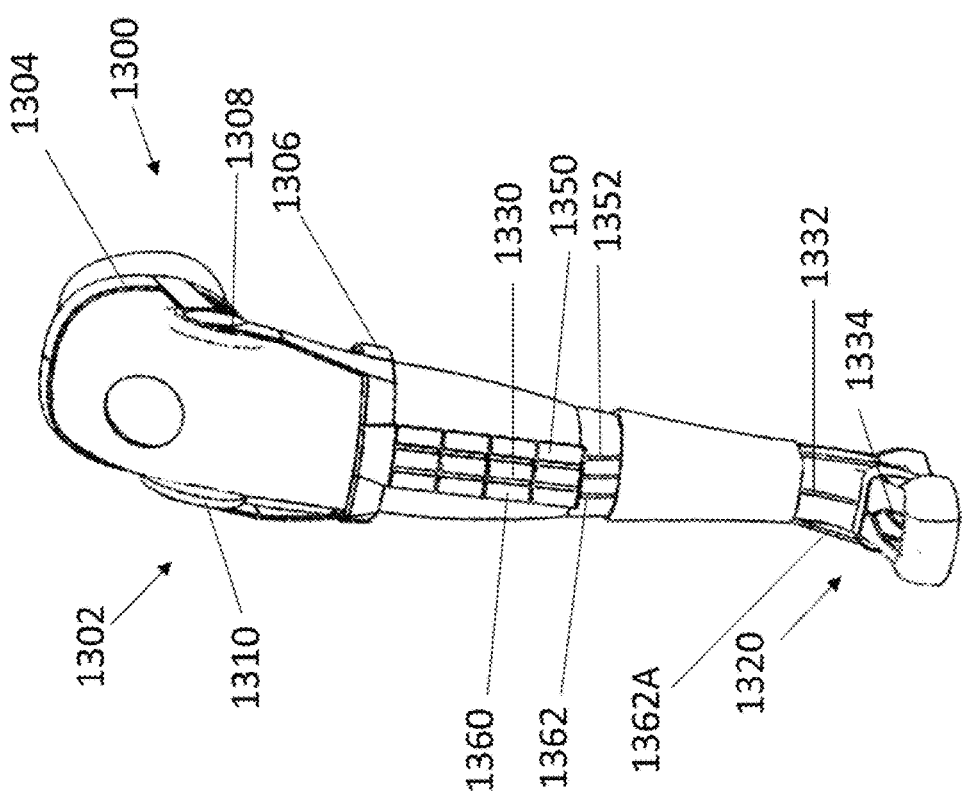
Figure 13D:
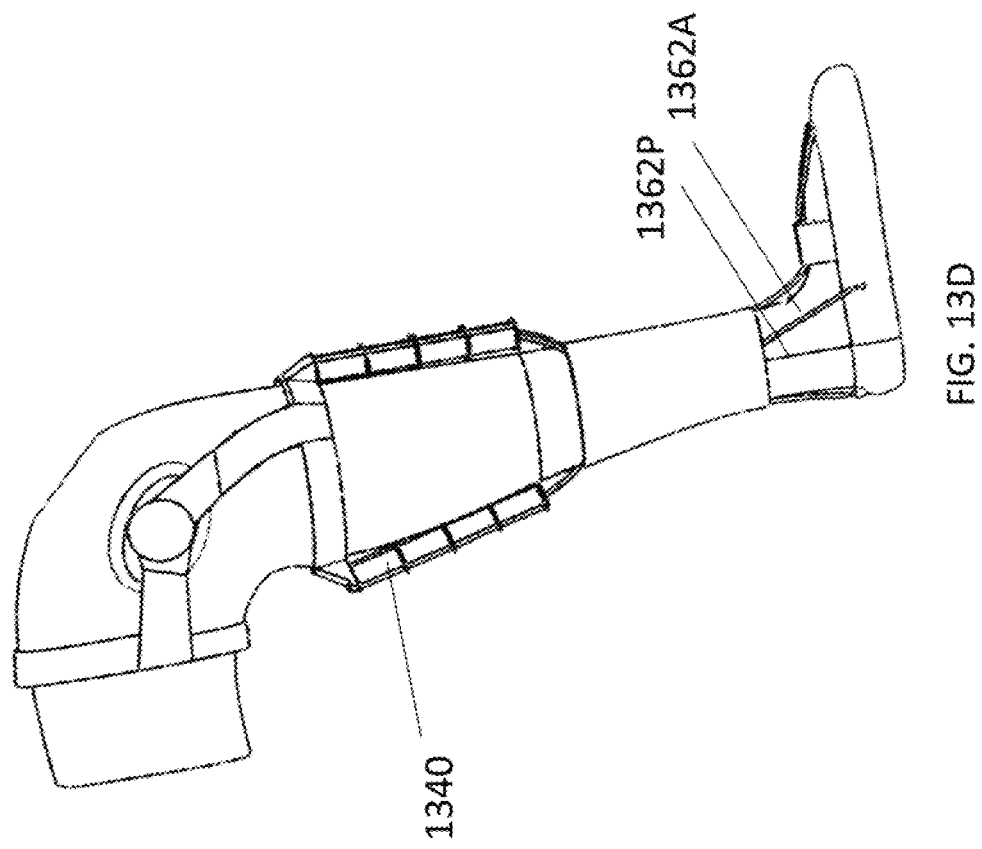
Figure 13C:
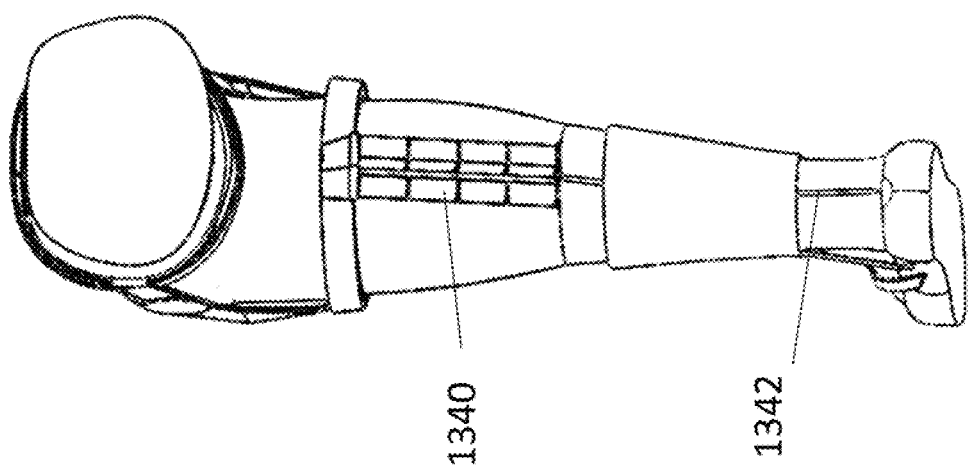

The tension member 1332 attached to actuator 1330 is attached to a position on top of the user's foot, as depicted in FIG. 13A to an area near the toecap 1334 at multiple (four) attachment points, after branching into four branches. In other embodiments, 1332 may be connected to strap 1370 such as via a harness such housing 55, depicted in FIG. 5, as described further herein. In still other embodiments, tension member 1332 may not branch at all, or may branch into fewer or more than four branches. Tension member 1352 is attached to an anterior, medial location of the footplate. Tension member 1362 branches into a first branch 1362A attached to an anterior, lateral location of the footplate and a second branch 1362P attached to a posterior, lateral location of the footplate. Tension member 1342 is attached to a posterior, central location of the footplate.

Footplate 150 depicted in FIGS. 14A and 14B depicts a plurality of holes for receiving tension members. Hole 142 receives tension member 1352 attached to inversion MASM actuator 1350. Hole 144 receives tension member 1362 attached to eversion MASM actuator 1360. Heel support 146 comprises one or more holes for receiving tension member 1342 attached to plantarflexion MASM actuator 1340. Slots 148 on opposite sides of the footplate are for receiving a strap (e.g. 1370 shown in FIG. 13B) that extends across the instep of the shoe. Holes 152 on opposite sides of the footplate positioned outward of slots 148 are for receiving a plurality of wire members for reinforcing the strap. Strap 1370 thus is disposed between the wire members and the top of the wearer's foot, also protecting the wearer from the cables rubbing against the wearer's skin.

Referring now to FIG. 5, housing 55 is depicted as an exemplary design for mounting on the instep strap for anchoring tension member 1332, connected to dorsiflexion MASM actuator 1330, to the footplate. Housing 55 includes a slot 52 for receiving the instep strap (e.g. 1370) and a seat 54 for receiving a one or more clamping units (e.g. 40, 42) comprising one or more clamps (e.g., 43A, 43B, 43C). In view of the three holes 152 depicted on footplate 150, a suitable clamping unit for use in connection with housing 55 for use on the instep may comprise a clamping unit having at least three clamps, each clamp configured to receive one or more wires from either or both sides of the footplate. Wires may be mounted to each hole on the footplate such that each clamp receives a wire from both sides, or six clamps may be provided with each receiving only one wire from one side. Wires may be mounted to all or fewer of the holes on each side, and more or fewer holes may be provided for mounting the wires. The wires provide adjustability and firmness for transmitting the forces to the footplate from the housing, whereas the strap provides cushioning for the instep of the wearer. Hole 56 receives the distal end of tension member 1332, thus connecting dorsiflexion MASM actuator 1330 to the footplate via the cables adjustably secured within housing 55.

Figures 1, 15B:
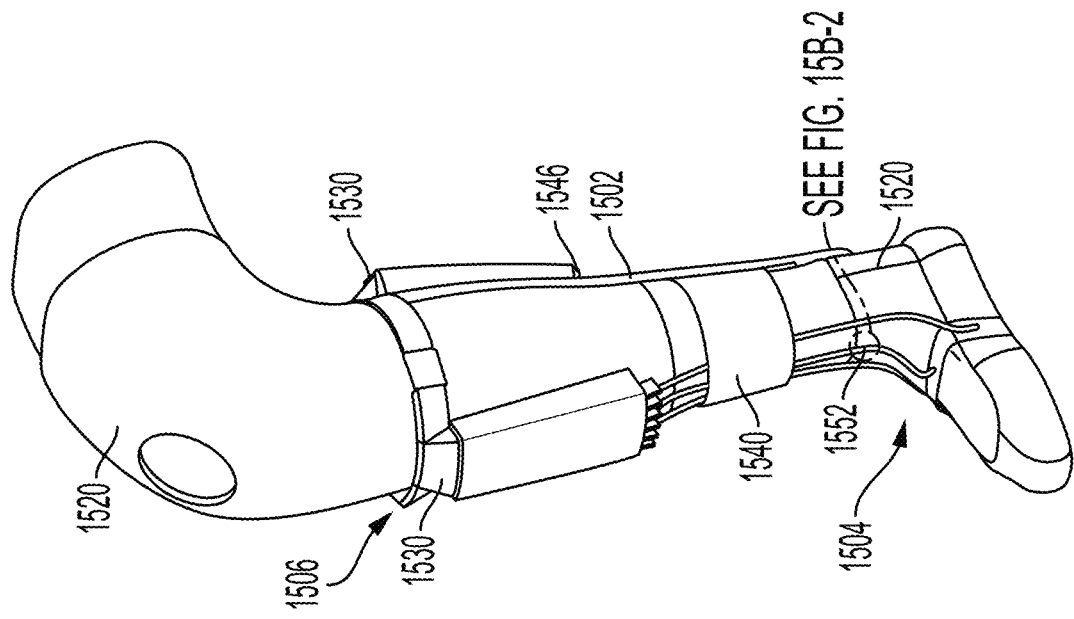
Figure 15A:
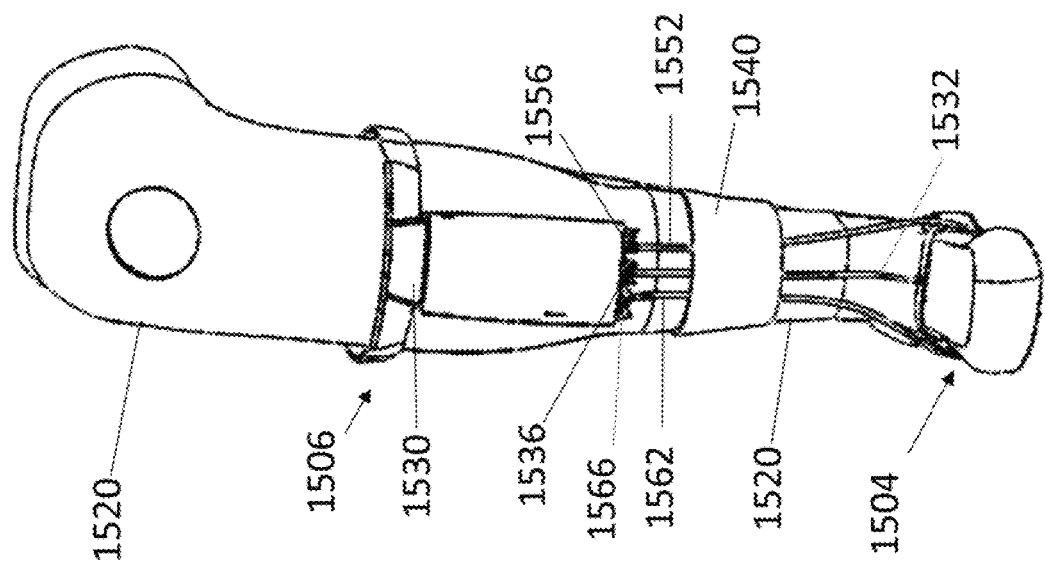
FIG. 15A schematically illustrates a front view of a second exemplary ankle exoskeleton embodiment.
Figures 2, 15B:
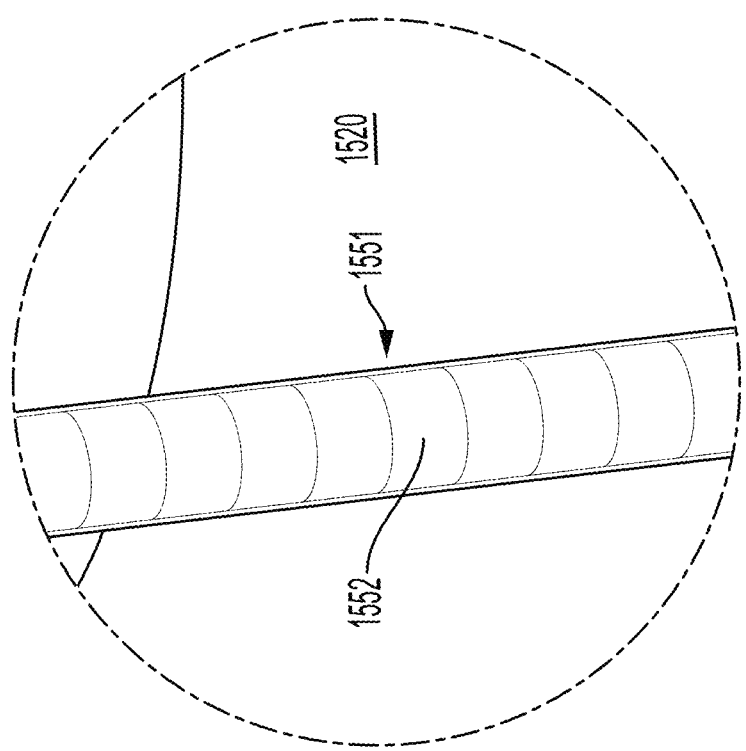

Slot 154 is configured to receive the distal end of a connecting member for another powered exoskeleton embodiment for mounting about an ankle depicted in FIGS. 15A-15D. Unlike the embodiment depicted in FIGS. 13A-13D, in which the distal and proximal portions of the exoskeleton are not connected to one another by frame elements, the embodiment depicted in FIGS. 15A-15D includes an exoskeletal connector 1502 that extends between the distal portion 1504 of the frame (e.g. footplate 150) and the proximal portion 1506 of the frame. Connector 1502 may be a rod-type structure, sometimes referred to as the "back-rod." The exoskeletal connector 1502 is affixed to a lateral connection point on the footplate (e.g. slot 154) and to a posterior, medial connection point 1510 on the proximal portion of the frame. Connector 1502 extends between the connection points posterior to the lower leg of the user, as best depicted in FIG. 15D. Although shown in a particular configuration in FIGS. 15A-15D, it should be understood that the connection points for the exoskeletal connector to the footplate and to the proximal portion of the frame are not limited to any particular locations or relative locations (e.g. medial, lateral, posterior, anterior) and the connector may extend along any portion of the lower leg of the user.

In the embodiments depicted in FIGS. 15A-15D, each of the MASM actuator assemblies are configured to move freely in a pocket 1580, 1590 formed in or attached to a textile member 1520 (e.g. a sock), and are configured to be removably anchored at their proximal ends to the proximal portion of the frame. For example, connection mechanisms 1530 located where the MASM actuator assemblies are anchored to the proximal portion 1506 of the exoskeleton may comprise mating interlocking (e.g. male/female) connectors, which may be held in place by any means known in the art, including but not limited to the use of biased tabs and slots that create a snap-fit, magnetic connectors, or the like. As shown in FIGS. 15A-15D, the sock extends above the user's knee. Ideally, however, the connections can be snapped into place after the user threads his or her leg through the sock. Preferably, each respective tension member is confined for some portion of its length within relatively low friction conduits. The low friction conduit may comprise a tube, such as comprised of ultrahigh molecular weight (UHMW) polyethylene or other lining, that provides low friction to allow the cables to move up and down freely, but with sufficient side-to-side anchoring to minimize or prevent side-to-side displacement and rubbing against the wearer's skin. Cuff 1540, disposed over the tubes, minimizes bowing of the tension members. Instead of cuff 1540, the wire conduits may be attached to (e.g. sewed into) the sock 1520 and may be less visibly defined than as depicted in the figures (for emphasis). The low friction conduits may extend nearly the entire length of the tension members between connection points to the MASM and the exoskeleton (i.e. as will be well understood by one of skill in the art, each of the elements referred to as "tension members" in FIGS. 13A-D (e.g. 1332, 1342, 1352, 1362, 1362A, 1362B) and FIGS. 15A-D (e.g. 1532, 1542, 1552, 1562) may actually depict the conduits in which the tension members are disposed, with the tension members themselves not visible through the walls of the conduit. The conduits may be individually formed within the textile sock (e.g. 1520) rather than part of a cuff (e.g. 1540). An exemplary depiction of a tension member 1552 inside a conduit 1551 in textile member 1520 is shown in the longitudinal section view FIG. 15B-2.

Housings 1536, 1546, 1556, 1566, similar to 1222 referenced in FIG. 12B, are located at the distal end of each MASM (hidden within pockets 1580, 1590, but similarly positioned to MASMs 1330, 1340, 1350 and 1360, respectively, as depicted in FIGS. 13A-13D). Each housings holds one or more clamping units (e.g. 40, 42) with at least one clamp (e.g. 43A) that permits adjustment of the length (and tension) of the respective tension members (1532, 1542, 1552, 1562) at their respective proximal ends. The distal ends of the tension members are typically non-adjustably fixed to the footplate.

Figure 18:
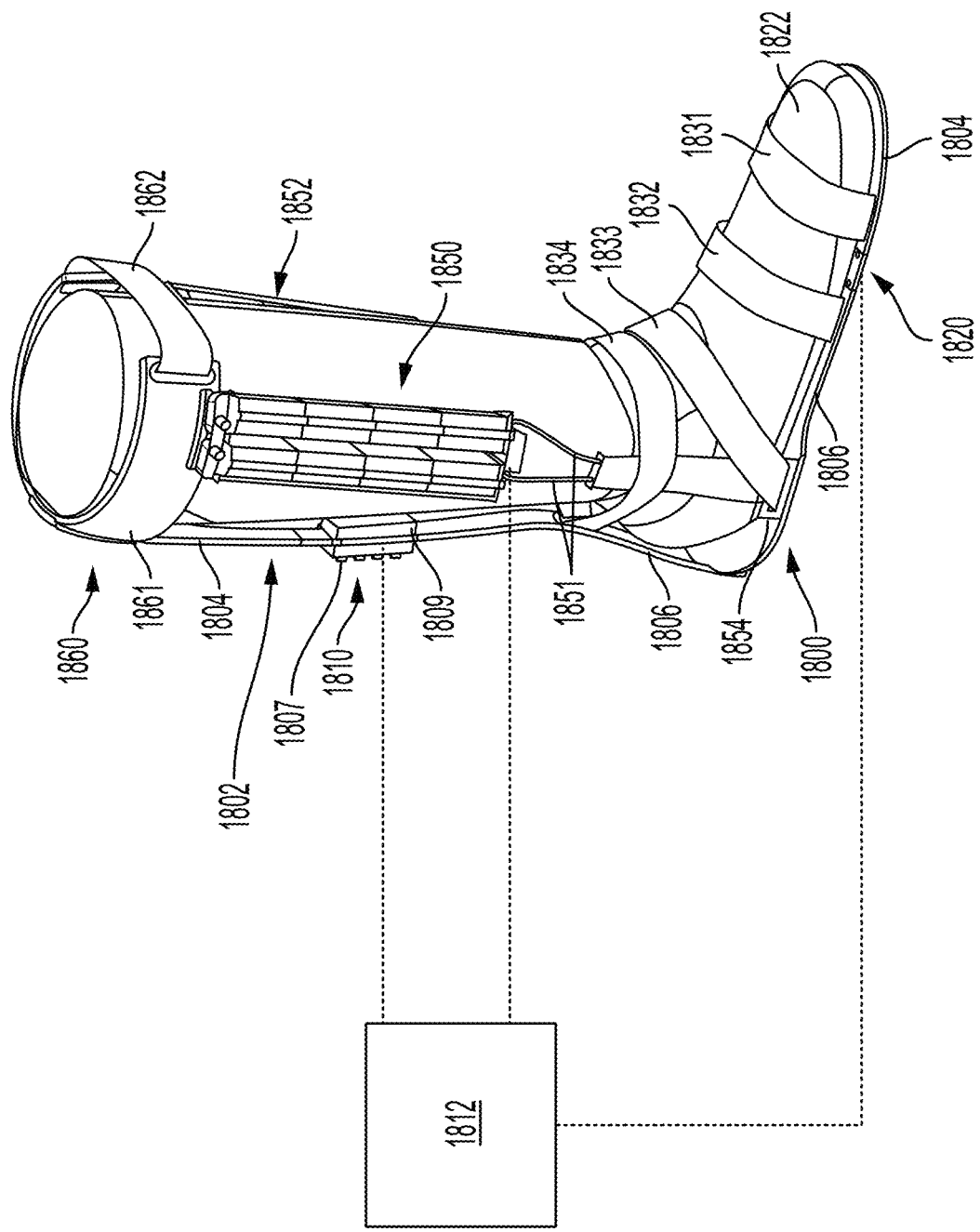
FIG. 18 schematically illustrates a third exemplary ankle exoskeleton embodiment.

In another exemplary embodiment, depicted in FIG. 18, the powered exoskeleton may comprise an ankle-foot orthotic (AFO) having a back-rod 1802 extending from footplate 1800 to the proximal portion 1806 of the frame. The back-rod in an AFO supports the patient's shank, and may provide passive assistance to patients during walking. In the embodiment depicted in FIG. 18, back-rod 1802 is a smart back-rod having an adjustable stiffness. Stiffness of the back-rod can thus be adjusted based on various factors such as the wearer's weight and level of assist or support she/he may need during gait. In some designs, this stiffness may be adjusted to a fixed parameter for each wearer. In preferred embodiments, however, the stiffness is adaptable to the user's gait and conforms to a stiffness profile during each stride. For example, each gait cycle (two consecutive footsteps) includes at least seven different phases, during which the degree of support or assistance of the back-rod may slightly change in accordance with active adjustments of the stiffness of the smart back-rod during the subject's gait. In one embodiment depicted in FIG. 18, back-rod 1802 includes an intermediate soft actuator 1810 (such as a stacked dielectric elastomer as described herein) integrated into the back-rod connected to controller 1812. The controller is configured to modulate stiffness of this actuator 1810 in synchrony with each phase of gait, by modulating the electrical power drawn by the actuator. The use of a smart, dynamic back-rod has been found to significantly improve performance of AFOs relative to AFOs with a static back-rod, as confirmed through patient and practitioners interviews. Controller 1812 may be connected to a sensor and processor (not shown in FIG. 18, to reduce clutter) for detecting phase of gait, as generally described herein and as depicted in FIG. 15C.

As also depicted in FIG. 18, footplate 1800 may also comprise a joint 1820 in the general region of the darkened portion of the footplate as indicated, preferably under the metatarsal joint of the wearer's foot 1822. Joint 1820 allows for the wearer's foot to flex while the wearer is pushing off the ground, before swinging the corresponding leg forward. Footplates having such a joint provide for better clearance of the foot relative to footplates without, thereby reducing the risk of fall, and increasing the efficiency of walking. Presence of a footplate joint 1820 also allows for more natural ankle motion and gait, and thereby reduces potential adverse neural adaptation and disuse atrophy of the muscles around the ankle associated with the use of conventional AFOs having no such joint in the footplate. Joint 1820 may comprise a soft actuator (such one or more dielectric elastomer units, as described herein) having variable and controllable stiffness attached to controller 1812. The controller may be configured to modulate the stiffness of the joint to provide a different level of assist and support for the foot tailored to characteristics of the wearer and/or dependent upon and synchronized with phase of gait.

Because fitting an AFO in the shoe of a wearer can be a major challenge for the general population of wearers who benefit from the use of such an AFO, the back-rod 1802 may be readily attachable and detachable, allowing users to keep the foot-plate inside the shoe and then attach/detach the rest of the brace during donning/doffing the orthosis. For example, back-rod 1802 may comprise a distal end having a male, connector configured to mate with a female connector mounted in footplate 1800, or vice versa. One or both of the connector portions may have spring-loaded features configured to secure the connectors together when fully inserted, or may include cam-driven clamps and associated attachments prongs on the footplate and/or back-rod to permit connection and disconnection. Such mechanisms are well known to those of skill in the art, such as may be associated commonly with phone jack mechanisms, toggle latch clamps, or the like. The invention is not limited to any particular arrangement of connection/disconnection features.

An AFO with a stiffness-adjustable joint in the footplate may have utility in AFOs of any type, beyond the powered exoskeleton embodiments as described herein. Accordingly, an exemplary AFO may comprise any frame having at least a proximal frame portion configured to be removably attached to a user proximal an ankle joint of the user and connected to a footplate configured to be secured beneath a foot of a user and having a joint with adjustable stiffness positioned to align with a metatarsal joint of the user's foot. In accordance with the exemplary embodiment depicted in FIG. 18, the adjustable stiffness may be provided by one or more dielectric elastomer units proximally anchored to a proximal portion of the footplate and distally anchored to a distal portion of the footplate. The proximal and distal portions of the footplate are typically inflexible. The joint is connected to a controller configured modulate stiffness of the one or more dielectric elastomer units by modulating power to the one or more integrated dielectric elastomer units.

In the exemplary embodiment depicted in FIG. 18, the footplate is secured to the user by a plurality of straps, including strap 1831 attached at opposite ends to distal portion 1804 of the footplate, strap 1832 attached at opposite ends to proximal portion 1806 of the footplate, strap 1834 attached at opposite ends to back-rod 1802 posterior the ankle and disposed across the user's foot anterior of the ankle, and strap 1833 attached to a lateral MASM actuator 1850 at one end and to a medial MASM actuator 1852 on an opposite end (not shown). As depicted, MASM actuator 1852 is a 2×4 MASM comprising two parallel sets of four DEA units in series, with each set of four DEA units having a tension member 1851 extending between strap 1833 and the MASM. Between connections to the lateral and medial MASM actuators, strap 1833 is threaded through and slidably supported by a corresponding lateral guide 1854 anchored to the lateral side of the footplate, disposed across the user's foot anterior to the user's ankle, and threaded through and slidably supported by a corresponding medial guide (not shown) anchored to the medial side of the footplate. Some or all of the straps may be integrated into, or replaced by members of, an article of footwear, such as a shoe or sock, configured to secure the footplate to the user's foot.

Back-rod 1802 comprises a proximal portion 1804 connected to calf band 1860, a distal portion 1806 connected to footplate 1800, and MASM actuator 1810 comprises an anterior MASM module 1807 and a posterior MASM module 1809, anchored to the back rod. In one embodiment, the proximal and distal portions of the back rod may be discrete and separate portions, with a gap between them, in which the MASM actuator is connected at opposite ends to the proximal and distal portions of the back rod. In other configurations, the back-rod may comprise a single continuous component, wherein the MASM actuator serves as additional mass with variable stiffness. In embodiments with discrete portions, at maximum stiffness, MASM actuator 1810 may provide a contracted connection between proximal portion 1804 and distal portion 1806 of the back rod 1802 with minimal distance between the respective portions and/or requiring a maximum amount of force to pull the respective portions apart, and at minimum stiffness MASM actuator 1810 may provide an elongated connection between proximal portion 1804 and distal portion 1806 of back rod 1802 with maximum distance between the respective portions and/or requiring a minimum amount of force to pull the respective portions apart. In embodiments with a single-piece back-rod, variations in stiffness may flex or bend the back-rod or modulate the amount of force necessary to bend or flex the back-rod and/or may isometrically provide changes in stiffness without contracting or elongating. Calf band 1860 may comprise a non-flexible, non-adjustable portion 1861 that envelops only a portion (typically more than half) of the periphery of the wearer's calf, and to which the respective medial and lateral MASM actuators are attached, and a flexible and/or adjustable portion 1862 that is attachable and detachable from the non-flexible, non-adjustable portion 1861 on at least one end, to permit the AFO to be removably secured to the user's leg.

Although depicted and described herein with respect to the back-rod and footplate, one or more MASM actuators or dielectric elastomer units may be connected to any portion of an AFO or other exoskeleton frame and to a controller to effect variable stiffness. The variable stiffness may be set to a static value tailored to a user or may be dynamic and controlled based upon motion of the user, such as based upon phase of gait.

Exoskeletons for Gait Rehabilitation

The MASM-powered exoskeletons as described herein may be useful for any type of use, including rehabilitative or therapeutic uses for normally healthy subjects recuperating from injuries, and for any type of individual (adults or children), but particularly useful embodiment may include frames configured for removable attachment to a pediatric user, and in particular, for use by children with CP. In one embodiment, the exoskeletons may be controlled using gait phase detection (GPD) for triggering functional electrical stimulation (FES) in rehabilitation systems.

Typical gait has been described as a series of seven contiguous phases: Loading Response (LR), Mid-Stance (MSt), Terminal Stance (TSt), Pre-Swing (PSw), Initial Swing (ISw), Mid-Swing (MSw), and Terminal Swing (TSw). Methods for detecting these phases during walking, known as gait phase detection (GPD), are known and have been well documented with respect to healthy subjects. See, e.g., Behboodi, A. et al., "Seven phases of gait detected in real-time using shank attached gyroscopes", *Proceedings of the Proceedings of the Annual International Conference of the IEEE Engineering in Medicine and Biology Society*, EMBS; Milan, Italy, 2015; Vol. 2015-November, pp. 5529-5532, incorporated herein by reference. The foregoing method comprises a simple two-gyroscope GPD system that detects all seven phases of gait.

Figures 16A, 16B:
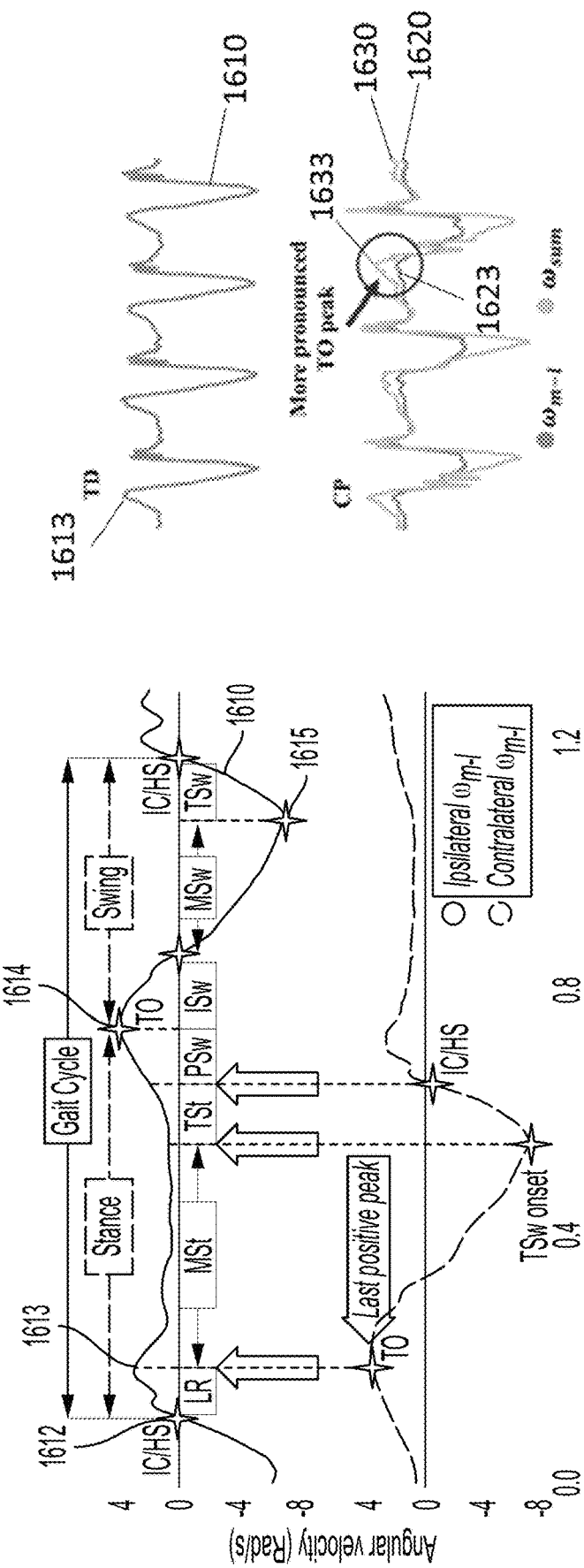
FIG. 16A illustrates a typical gait cycle for a healthy individual as measured by an IMU mounted on the shank of a subject.
FIG. 16B illustrates typical gait cycles for a typically developing (TD) child, a child with cerebral palsy (CP), and a curve showing the sum of all three axes of a gyroscope IMU mounted on a shank of a subject.

Exemplary GPD systems for identifying specific gait events for triggering FES to enhance gait in children with CP benefit from the use of a modified algorithm as compared to that previously described. For healthy adults and typically developing (TD) children, medio-lateral shank angular velocity ($\omega_{ml}$) has a definitive pattern 1610 during the gait cycle, as depicted in FIGS. 16A and 16B. The typical pattern comprises three positive peaks 1612, 1613, 1614 in the stance phase followed by a deep negative peak 1615 in the swing phase. This pattern is typically detected by attaching an inertial measurement unit (IMU), such as a gyroscope that measures angular velocity, to the shank of the subject. An exemplary IMU 10 suitable for this purpose may include an IMU made by APDM Inc., Portland, OR, USA, contain three-axis accelerometers, gyroscopes and magnetometers, and is depicted schematically as sensor 10 in FIG. 15C (but omitted in other figures to reduce clutter). Although some IMU devices may comprise a combination of accelerometers, gyroscopes and magnetometers measuring all relevant degrees of freedom, unless expressly stated, the term "IMU" as used herein does not imply a specific combination of sensors, and may refer to units comprising only an accelerometer, only a gyroscope, or only a magnetometer (or some combination of two of the foregoing), and may also refer to units configured to measure in only a single degree of freedom or in any combination of degrees of freedom fewer than all of those relevant in the measured system. One IMU (or gyroscope) is preferably attached to the lateral side of each shank of the subject with the Z-axis of the IMU aligned in the medio-lateral direction (i.e., axis of rotation of the knee in the sagittal plane), and the z-component of the gyroscope data ($\omega_{ml}$) is used as an input to the GPD system (e.g. controller 39). The IMUs may be aligned such that knee flexion and extension resulted in respective positive and negative values of $\omega_{ml}$.

The GDP-TD algorithm (used for typically developing children) was tested on children with CP. Although children with CP do not often exhibit typical gait events (e.g., those with equinus gait may lack heel strike), shank angular velocity shows similar features and can still be used to determine gait phases. However, some modifications to the GPD algorithm were found to be beneficial. In particular, while $\omega_{ml}$ typically has easily identifiable peaks and zero-crossings, the lack of a distinct peak at toe-off/end-contact (TO/EC) confounded ISw detection for children with CP. This issue was mitigated by using the arithmetic sum of all three components of shank angular velocity ($\omega_{sum}$) instead of to detect the TO/EC peak. The summed signal featured a more prominent peak at TO/EC, isolating it from spurious peaks present in the signal. Because $\omega_{sum}$ slightly leads $\omega_{ml}$ in time and because the MSw zero-crossing closely follows TO/EC, $\omega_{sum}$ was also used to detect the MSw zero crossing. This reduced the chances of erroneously detecting MSw (in $\omega_{ml}$) before detecting ISw (in $\omega_{sum}$).

The foregoing is now illustrated with respect to FIGS. 16A and 16B. Lines 1610 in FIGS. 16A and 16B depicts shank angular velocity about the medio-lateral axis ($\omega_{ml}$) for typically developing children and healthy adults during treadmill walking. Gait phase onset is based on the indicated peaks and zero-crossings. Four gait phase events are detected using ipsilateral shank angular velocity (loading response (LR), initial swing (ISw), mid-swing (MSw) and terminal swing (TSw). The three remaining gait phase events are detected using contralateral shank angular velocity (mid-stance (MSt), terminal stance (TSt) and pre-swing (PSw)). The onset of LR corresponds to initial contact (IC)/heel strike (HS) and the onset of ISw corresponds to toe-off/end-contact (TO/EC). IC may also be considered a separate phase from LR onset. The gait phase detection system as referenced herein is capable of splitting LR into an IC phase and LR. In such configurations, the IC phase may be identified as the current LR onset (zero-crossing) to the first positive peak 1612. FIG. 16B illustrates a comparison of line 1610, which depicts representative shank angular velocity about the medio-lateral axis for a typically developing (TD) child (top), to line 1620, which depicts representative shank angular velocity about the medio-lateral axis for a child with cerebral palsy (CP). A distinct peak 1613 is visible at the onset of ISw (TO/EC) in TD subjects while the peak 1623 is less distinct in CP subjects. The sum of all three components of shank angular velocity ($\omega_{sum}$) in line 1630 shows a more distinct peak at ISw onset 1633, and was used for ISw detection in children with CP.

Even with the increased detection reliability of ISw with $\omega_{sum}$, extraneous peaks and zero-crossings due to spasticity may result in false detections of ISw and MSw. To mitigate this, the following criteria were found to be beneficial:

(1) ISw detection was blocked until at least 60% of the average gait cycle duration had elapsed since the last LR detection,
(2) MSw detection was blocked until at least of 25% of the average of the last 10 gait cycle durations had elapsed since ISw; and
(3) peak detection threshold values were set to 25% of the smallest ISw peak height and highest TSw valley depth observed over the first few previous gait cycles.

Figure 17:
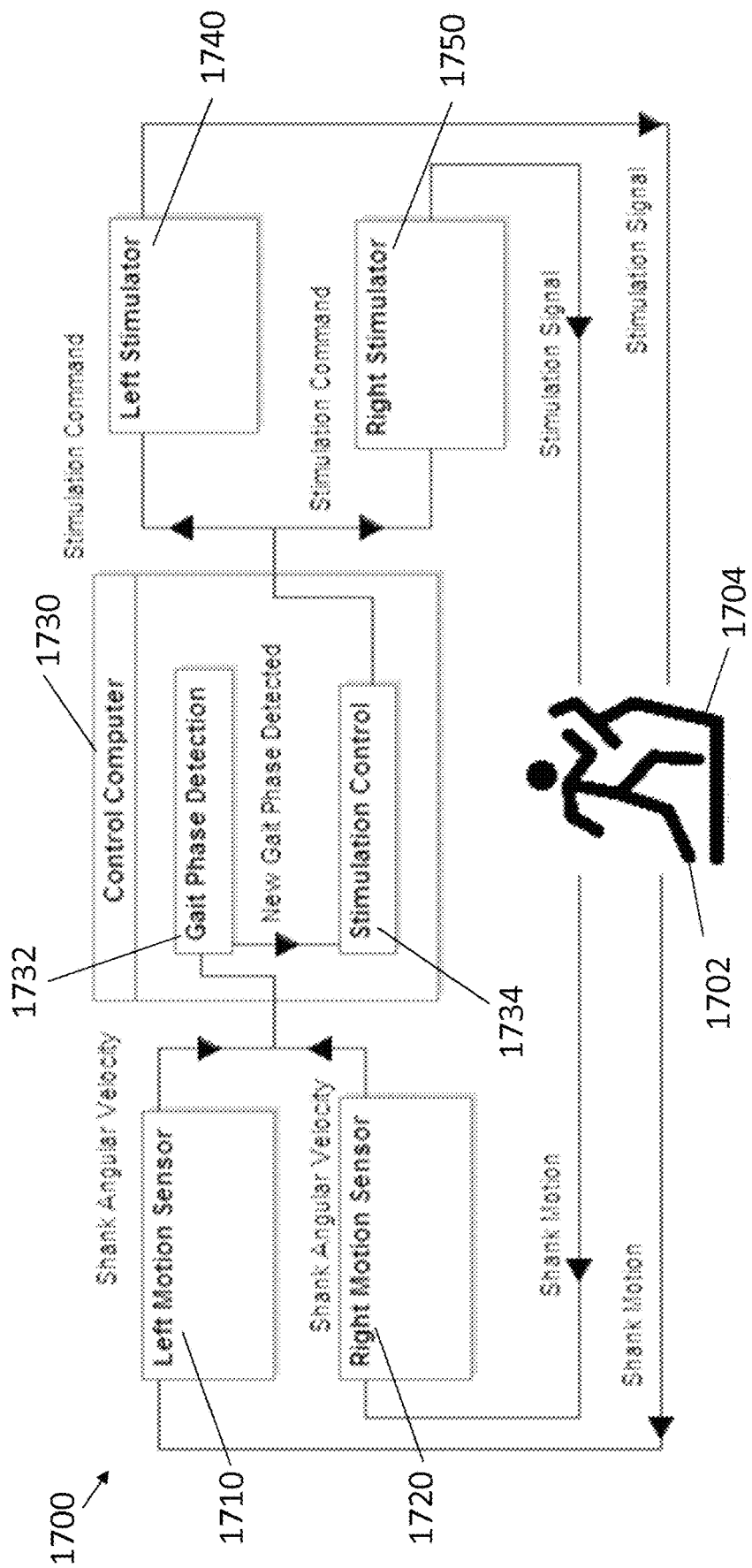
FIG. 17 schematically illustrates a control system for use with a gait phase detection (GPD) equipped controller for an MASM powered exoskeleton.

Thus, controller 39 may comprise a finite state control system including one or more feedback sensors 10 (e.g. which, for purposes of describing this embodiment, may be an IMU mounted on the lateral side of each exoskeleton for each leg) configured to activate a preset sequences of the plurality of MASM actuators (disposed in pockets 1580, 1590) in response to specific detected system state conditions. As depicted in FIG. 15C, pocket 1590 may comprise a plurality of actuators, including actuators for dorsiflexion, eversion, and eversion. In particular, data from IMU sensor 10, processed by processor 12 (which may be separate from or integral with controller 39, may be configured to detect different phases of ankle motion during a walking gait of the user, and the controller may further comprise plurality of stimulators for activating preset sequences of the plantarflexion, dorsiflexion, inversion, and eversion MASM actuators in synchrony with the detected phases of the walking gait, as illustrated schematically in the block diagram 1700 shown in FIG. 17. As depicted in FIG. 17, a subject 1702 walks on a treadmill 1704 with motion sensors 1710, 1720 attached to each of the left and right shanks. The motion sensors send shank angular velocity measurements to a control computer 1730. A gait phase detection algorithm 1732 detects gait phase transitions based on shank angular velocity. Upon gait phase transition, a stimulation control algorithm 1734 sends stimulation commands (indicating current amplitude and pulse duration) to left and right stimulators 1740, 1750 based on the subject's stimulation protocol. Systems without inversion and eversion MASM actuators may similarly activate only plantarflexion and dorsiflexion MASM actuators. In preferred embodiments, IMU sensor 10 comprises a gyroscope configured to detect bilateral shank angular velocity of the user for determining gait phase transitions. For powered exoskeletons configured for therapeutic use in connection with pediatric subjects with cerebral palsy, the controller may be configured with an algorithm for detecting gait phase based upon bilateral shank angular velocity about the z-axis, or based upon a sum of the bilateral shank angular velocity about all three axes of the gyroscope (depending upon the degree of CP and/or phase being detected), and the GPD detection algorithm in the processor may include detection criteria tailored to gait phase transitions of children with cerebral palsy. As described above, the detection criteria tailored to gait phase transitions of children with cerebral palsy may be generally described as including a delay in Initial Swing (ISw) detection until after a predetermined percentage of elapsed gait cycle, a delay in Mid-Swing (MSw) detection until a predetermined number of samples after ISw, and a peak detection threshold for ISw set to a predetermined percentage of a smallest detected peak in a predetermined number of cycles, with a peak detection threshold for Terminal Swing (TSw) set to a predetermined percentage of a smallest detected valley in a predetermined number of cycles. Some of the phases may only need to use angular velocity about the z-axis, whereas ISw and MSw may need to use summation of angular velocities, depending on the severity of the cerebral palsy of the individual user.

One distinctive aspect of MASM actuators is the elastomeric nature that closely mimics the passive elastic component of biological muscles. This can be modulated by the elastic silicone cover with various thickness and stiffness. For example, during TSw, the plantarflexion actuators may produce a significant amount of passive force by contracting eccentrically, which force is released during the push off phase PSw. This helps in generating a substantial amount of propulsive force for pushing the center of mass of the body forward during walking gait.

Although described with respect to specific types of exoskeleton embodiments, it should be understood that the invention is not limited to any particular uses for the MASM actuators as described herein. Furthermore, although emphasized for use in connection with elbow and ankle joints, the exoskeletons using MASM actuators may have utility for use in connection with any joint. Although discussed herein with respect to therapeutic or rehabilitative uses, exoskeletons as described herein are not limited to any particular uses. Aspects of the invention include any methods of using MASM actuators, exoskeletons, and/or AFOs as described herein.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A modular artificial skeletal muscle (MASM) actuator, the MASM actuator comprising:
   a plurality of dielectric elastomer units assembled in series or in parallel;
   a proximal anchoring member connected to a proximal end of at least one proximal dielectric elastomer unit and configured for attachment to a proximal anchor point relative to a user;
   a tension member having a proximal end attached to a distal end of at least one distal dielectric elastomer unit and a distal end configured for attachment to a distal anchor point relative to the user;
   a controller attached to a power source and to the plurality of dielectric elastomer units, the controller configured to cause simultaneous contraction or expansion of plurality of dielectric elastomer units, which contraction or expansion causes displacement of the tension member; and
   wherein the plurality of dielectric elastomer units is disposed in a pocket that is attached to a textile member, and each respective tension member is confined for some portion of its length within a conduit in the textile member.

2. The MASM actuator of claim 1, further comprising a flexible, low friction covering disposed over an external surface of the plurality of dielectric elastomer units.

3. The MASM actuator of claim 1, further comprising a self-sensing circuit connected to the controller, the self-sensing circuit configured to detect a relative longitudinal state of at least one sensed dielectric elastomer unit in the MASM and to provide feedback to the controller, wherein the controller is configured to control contraction or expansion of the plurality of dielectric elastomer units based upon the detected relative longitudinal state of the at least one sensed dielectric elastomer unit.

4. The MASM actuator of claim 3, wherein the controller comprises a proportional-integral-derivative (PID) controller.

5. The MASM actuator of claim 1, further comprising an electromyographic (EMG) signal processing interface connected to the controller and to one or more EMG sensors configured to detect electrical activity of a living muscle, wherein the controller is configured to control contraction or expansion of the plurality of dielectric elastomer units based upon a signal from the EMG signal processing interface.

6. The MASM actuator of claim 1, wherein the tension member comprises a flexible, non-extendable cable.

7. A powered exoskeleton configured to be worn by a user, the powered exoskeleton comprising:
   a frame comprising at least an proximal portion configured to be removably attached to the user proximal a joint of the user, a distal portion configured to be removably attached to the user distal of the joint of the user, the proximal and distal portions configured to move relative to one another with at least one degree of freedom;
   one or more modular MASM actuators of claim 1, each MASM actuator proximal anchoring member attached to the proximal portion of the frame at the proximal anchor point, each MASM actuator tension member distal end attached to the distal portion of the frame at the distal anchor point, each tension member having an adjustable length between the proximal anchor point and the distal anchor point, and the plurality of dielectric elastomer units of each MASM actuator is configured to be removably anchored to the proximal portion of the frame;
   wherein the displacement of the respective tension member caused by contraction or expansion of each MASM actuator causes corresponding displacement of the distal portion of the frame relative to the proximal portion of the frame.

8. The powered exoskeleton of claim 7, wherein the frame is configured for placement about an elbow joint of the user.

9. The powered exoskeleton of claim 8, wherein the frame proximal portion is configured to be anchored about a shoulder of the user and the frame distal portion comprises a cuff configured to be anchored to a forearm of the user.

10. The powered exoskeleton of claim 7, wherein the at least one tension member is connected to a displacement magnification system that converts a first amount of displacement of the tension member into a greater amount of displacement of the distal portion of the frame relative to the proximal portion.

11. The powered exoskeleton of claim 7, wherein the frame is configured for removable attachment to a pediatric user.

12. The powered exoskeleton of claim 7, wherein the frame is configured for placement about an ankle joint of the user.

13. The powered exoskeleton of claim 12, wherein the proximal portion of the frame comprises a first portion configured to be mounted proximal of a knee of the user, a second portion configured to be mounted distal of the knee of the user, the first and second portions connected to one another on opposite sides of the knee of the user with opposite exoskeletal knee joints.

14. The powered exoskeleton of claim 7, comprising a plurality of MASM actuators.

15. The powered exoskeleton of claim 14, wherein the controller comprises a control system including one or more feedback sensors and is configured to activate preset sequences of the plurality of MASM actuators in response to specific detected system state conditions.

16. A powered exoskeleton configured to be worn by a user, the powered exoskeleton comprising:
   a frame configured for placement about an ankle joint of the user, the frame comprising a distal portion configured to be removably attached to the user distal of the joint of the user, the proximal and distal portions configured to move relative to one another with at least one degree of freedom;
   a plurality of modular artificial skeletal muscle (MASM) actuators, including at least one plantarflexion MASM actuator configured to augment ankle plantarflexor muscle function of the user and at least one dorsiflexion MASM actuator configured to augment ankle dorsiflexor muscle function of the user, the plurality of MASM actuators comprising:
      a plurality of dielectric elastomer units assembled in series or in parallel,
      a proximal anchoring member connected to a proximal end of at least one proximal dielectric elastomer unit and attached to the proximal portion of the frame at a proximal anchor point relative to a user,
      a tension member having a proximal end attached to a distal end of at least one distal dielectric elastomer unit and a distal end attached to the distal portion of the frame at a distal anchor point relative to the user, each tension member having an adjustable length between the proximal anchor point and the distal anchor point; and a controller attached to a power source and to the plurality of dielectric elastomer units, the controller configured to cause simultaneous contraction or expansion of plurality of dielectric elastomer units, which contraction or expansion causes displacement of the tension member, which displacement causes corresponding displacement of the distal portion of the frame relative to the proximal portion of the frame.

17. The powered exoskeleton of claim 16, further comprising at least one inversion MASM actuator configured to augment ankle inversion muscle function and at least one eversion MASM actuator configured to augment ankle eversion muscle function.

18. The powered exoskeleton of claim 17, wherein the controller comprises a control system including a sensor configured to detect different phases of ankle motion during a walking gait of the user and to activate preset sequences of the plantarflexion, dorsiflexion, inversion, and eversion MASM actuators in synchrony with the detected phases of the walking gait.

19. The powered exoskeleton of claim 18, wherein the sensor configured to detect different phases of ankle motion during the walking gait comprises a gyroscope configured to detect bilateral shank angular velocity of the user for determining gait phase transitions and a plurality of stimulators for activating the MASM actuators.

20. The powered exoskeleton of claim 19, wherein the powered exoskeleton is configured to rehabilitate a gait of a pediatric user with cerebral palsy, and the controller is configured with an algorithm for detecting gait phase based upon z axis bilateral shank angular velocity or a sum of bilateral shank angular velocity about three axes and which includes detection criteria tailored to gait phase transitions of children with cerebral palsy.

21. The powered exoskeleton of claim 20, wherein the detection criteria tailored to gait phase transitions of children with cerebral palsy includes a delay in Initial Swing (ISw) detection until after a predetermined percentage of elapsed gait cycle, a delay in Mid-Swing (MSw) detection until a predetermined number of samples after ISw, and a peak detection threshold for ISw set to a predetermined percentage of a smallest detected peak in a predetermined number of previous cycles, and a peak detection threshold for Terminal Swing (TSw) set to a predetermined percentage of a smallest detected valley in a predetermined number of previous cycles, wherein the peak for ISw is evaluated as a sum of the bilateral shank angular velocity about the three axes.

22. A powered exoskeleton configured to be worn by a user, the powered exoskeleton comprising:

a frame configured for placement about an ankle joint of the user, and comprising at least a proximal portion configured to be removably attached to the user proximal a joint of the user, a distal portion configured to be removably attached to the user distal of the joint of the user, the proximal and distal portions configured to move relative to one another with at least one degree of freedom, and the distal portion comprises a footplate configured for positioning beneath a foot of the user and comprises a joint positioned to align with a metatarsal joint of the user's foot; and one or more modular artificial skeletal muscle (MASM) actuators, the one or more MASM actuators comprising:

a plurality of dielectric elastomer units assembled in series or in parallel, a proximal anchoring member connected to a proximal end of at least one proximal dielectric elastomer unit and configured for attachment to a proximal anchor point relative to a user and to the proximal portion of the frame at the proximal anchor point, a tension member having a proximal end attached to a distal end of at least one distal dielectric elastomer unit and a distal end configured for attachment to a distal anchor point relative to the user and to the distal portion of the frame at the distal anchor point, the tension member further having an adjustable length between the proximal anchor point and the distal anchor point, and a controller attached to a power source and to the plurality of dielectric elastomer units, the controller configured to cause simultaneous contraction or expansion of plurality of dielectric elastomer units, which contraction or expansion causes displacement of the tension member, and the displacement of the tension member causes corresponding displacement of the distal portion of the frame relative to the proximal portion of the frame.

23. The powered exoskeleton of claim 22, wherein the footplate joint comprises one or more dielectric elastomer units connected to the controller, and the controller is configured to modulate stiffness of the footplate joint by modulating power to the one or more dielectric elastomer units.

24. The powered exoskeleton of claim 23, further comprising a control system including a sensor configured to detect different phases of ankle motion during a walking gait of the user and to modulate stiffness of the footplate joint based upon detected phase of gait.

25. The powered exoskeleton of claim 22, wherein the proximal portion of the frame is configured for positioning about a lower leg of the user and further comprises an exoskeletal connector connecting the footplate to a posterior, connection point on the proximal portion of the frame, and configured to extend along the lower leg of the user.

26. The powered exoskeleton of claim 25, wherein the exoskeletal connector is configured for detachment and reattachment to the footplate.

27. The powered exoskeleton of claim 26, wherein the exoskeletal connector comprises one or more integrated dielectric elastomer units connected to the controller, and the controller is configured to modulate stiffness of the exoskeletal connector by modulating power to the one or more integrated dielectric elastomer units.

28. The powered exoskeleton of claim 27, wherein the exoskeletal connector comprises a proximal exoskeletal connector portion connected to the proximal portion of the frame and a distal exoskeletal connector portion connected to the footplate, and the one or more integrated dielectric elastomer units are connected between the proximal exoskeletal connector portion and the distal exoskeletal connector portion.

29. The powered exoskeleton of claim 27, further comprising a control system including a sensor configured to detect different phases of ankle motion during a walking gait of the user and to modulate stiffness of the exoskeletal connector based upon detected phase of gait.

30. The powered exoskeleton of claim 25, wherein the exoskeletal connector has an adjustable stiffness.

31. The powered exoskeleton of claim 22, wherein the proximal portion of the frame is configured for positioning about a lower leg of the user and has no exoskeletal member connecting the footplate and the proximal portion of the frame other than the MASM actuators and tension members.

32. The powered exoskeleton of claim 22, further comprising a dorsiflexion MASM actuator configured to augment ankle dorsiflexor muscle function, wherein the tension member connected to the dorsiflexion MASM actuator connects to a housing mounted to an adjustable, cable-reinforced instep strap connected to opposite sides of the footplate.

33. An exoskeleton configured to be worn by a user, the exoskeleton comprising a plurality of members configured to be attached to the user and one or more dielectric elastomer units anchored to at least one member and connected to a controller configured to modulate power to the one or more dielectric elastomer units to control stiffness of the at least one member, and wherein the one or more dielectric elastomer units is disposed in a pocket that is attached to a textile member.

34. An ankle-foot orthotic (AFO) comprising a frame comprising at least a proximal frame portion configured to be removably attached to a user proximal an ankle joint of the user, the proximal frame portion connected to a footplate configured to be secured beneath a foot of a user, the footplate having a joint positioned to align with a metatarsal joint of the user's foot, wherein the joint comprises one or more dielectric elastomer units proximally anchored to a proximal portion of the footplate and distally anchored to a distal portion of the footplate, the joint connected to a controller configured modulate stiffness of the one or more dielectric elastomer units by modulating power to the one or more integrated dielectric elastomer units.

* * * * *